US011850011B2

(12) United States Patent
Staunton et al.

(10) Patent No.: US 11,850,011 B2
(45) Date of Patent: *Dec. 26, 2023

(54) TECHNIQUES FOR MODIFYING TOOL OPERATION IN A SURGICAL ROBOTIC SYSTEM BASED ON COMPARING ACTUAL AND COMMANDED STATES OF THE TOOL RELATIVE TO A SURGICAL SITE

(71) Applicant: MAKO Surgical Corp., Weston, FL (US)

(72) Inventors: Douglas Alan Staunton, Kalamazoo, MI (US); Paul Hoekstra, Kalamazoo, MI (US); Michael Dale Dozeman, Portage, MI (US)

(73) Assignee: MAKO Surgical Corp., Weston, FL (US)

( * ) Notice: Subject to any disclaimer, the term of this patent is extended or adjusted under 35 U.S.C. 154(b) by 48 days.

This patent is subject to a terminal disclaimer.

(21) Appl. No.: 17/534,499

(22) Filed: Nov. 24, 2021

(65) Prior Publication Data
US 2022/0079692 A1 Mar. 17, 2022

Related U.S. Application Data

(63) Continuation of application No. 15/840,278, filed on Dec. 13, 2017, now Pat. No. 11,202,682.
(Continued)

(51) Int. Cl.
*A61B 34/30* (2016.01)
*A61B 34/20* (2016.01)
(Continued)

(52) U.S. Cl.
CPC .............. *A61B 34/30* (2016.02); *A61B 34/20* (2016.02); *A61B 34/76* (2016.02); *A61B 34/77* (2016.02);
(Continued)

(58) Field of Classification Search
CPC ......... A61B 34/30; A61B 34/20; A61B 34/76; A61B 34/77; A61B 34/10; A61B 34/32;
(Continued)

(56) References Cited

U.S. PATENT DOCUMENTS 3,202,759 A   8/1965  Forgue
3,344,260 A   9/1967  Lukens, II
(Continued)

FOREIGN PATENT DOCUMENTS

CN   102208835 A   10/2011
CN   102470016 A    5/2012
(Continued)

OTHER PUBLICATIONS

Abovitz, R., Digital surgery the future of medicine and human-robot symbiotic interaction, Industrial Robot: An International Journal, 2001, pp. 401-406, vol. 28, Issue 5, Hollywood, FL, USA; 5 pages.
(Continued)

*Primary Examiner* — Jeff A Burke
*Assistant Examiner* — Kyle T Johnson
(74) *Attorney, Agent, or Firm* — Howard & Howard Attorneys PLLC

(57) ABSTRACT

A robotic surgical system and method of operating the same. A manipulator supports a tool that has a TCP and manipulates a target bone. A navigation system has a localizer to monitor states of the manipulator and the target bone. Controller(s) determine commanded states of the TCP to move the tool along a cutting path relative to the target bone to remove material from the target bone. The controller(s) determine actual states of the TCP responsive to commanded movement of the tool along the cutting path, wherein each one of the commanded states of the TCP has a corresponding one of the actual states of the TCP for a given time step. The controller(s) compare the corresponding commanded and
(Continued)

actual states of the TCP for one or more given time steps to determine a deviation and modify operation of the tool to account for the deviation.

18 Claims, 9 Drawing Sheets

Related U.S. Application Data

(60) Provisional application No. 62/435,254, filed on Dec. 16, 2016.

(51) Int. Cl.
*A61B 34/00* (2016.01)
*A61B 34/10* (2016.01)
*A61B 34/32* (2016.01)

(52) U.S. Cl.
CPC .............. *A61B 34/10* (2016.02); *A61B 34/32* (2016.02); *A61B 2034/104* (2016.02); *A61B 2034/105* (2016.02); *A61B 2034/2051* (2016.02); *A61B 2034/2055* (2016.02); *A61B 2034/2057* (2016.02); *A61B 2034/2059* (2016.02); *A61B 2034/2063* (2016.02); *A61B 2034/2072* (2016.02); *A61B 2034/2074* (2016.02); *Y10S 901/09* (2013.01)

(58) Field of Classification Search
CPC ........ A61B 2034/104; A61B 2034/105; A61B 2034/2051; A61B 2034/2055; A61B 2034/2057; A61B 2034/2059; A61B 2034/2063; A61B 2034/2072; A61B 2034/2074; Y10S 901/09
See application file for complete search history.

(56) References Cited

U.S. PATENT DOCUMENTS

| | | |
|---|---|---|
| 3,891,800 A | 6/1975 | Janssen et al. |
| 4,425,818 A | 1/1984 | Asada et al. |
| 4,442,493 A | 4/1984 | Wakai et al. |
| 4,561,749 A | 12/1985 | Utagawa |
| 4,564,819 A | 1/1986 | Hirose |
| 4,696,167 A | 9/1987 | Matsui et al. |
| 4,863,133 A | 9/1989 | Bonnell |
| 4,979,949 A | 12/1990 | Matsen, III et al. |
| 5,078,140 A | 1/1992 | Kwoh |
| 5,086,401 A | 2/1992 | Glassman et al. |
| 5,091,861 A | 2/1992 | Geller et al. |
| 5,154,717 A | 10/1992 | Matsen, III et al. |
| 5,184,024 A | 2/1993 | Hussmann et al. |
| 5,231,693 A | 7/1993 | Backes et al. |
| 5,279,309 A | 1/1994 | Taylor et al. |
| 5,299,288 A | 3/1994 | Glassman et al. |
| 5,339,799 A | 8/1994 | Kami et al. |
| 5,343,391 A | 8/1994 | Mushabac |
| 5,397,323 A | 3/1995 | Taylor et al. |
| 5,399,951 A | 3/1995 | Lavallee et al. |
| 5,408,409 A | 4/1995 | Glassman et al. |
| 5,434,489 A | 7/1995 | Cheng et al. |
| 5,445,144 A | 8/1995 | Wodicka et al. |
| 5,543,695 A | 8/1996 | Culp et al. |
| 5,562,448 A | 10/1996 | Mushabac |
| 5,569,578 A | 10/1996 | Mushabac |
| 5,576,727 A | 11/1996 | Rosenberg et al. |
| 5,629,594 A | 5/1997 | Jacobus et al. |
| 5,630,431 A | 5/1997 | Taylor |
| 5,682,886 A | 11/1997 | Delp et al. |
| 5,689,159 A | 11/1997 | Culp et al. |
| 5,691,898 A | 11/1997 | Rosenberg et al. |
| 5,695,500 A | 12/1997 | Taylor et al. |
| 5,699,038 A | 12/1997 | Ulrich et al. |
| 5,710,870 A | 1/1998 | Ohm et al. |
| 5,711,299 A | 1/1998 | Manwaring et al. |
| 5,721,566 A | 2/1998 | Rosenberg et al. |
| 5,730,129 A | 3/1998 | Darrow et al. |
| 5,731,804 A | 3/1998 | Rosenberg |
| 5,734,373 A | 3/1998 | Rosenberg et al. |
| 5,737,500 A | 4/1998 | Seraji et al. |
| 5,739,811 A | 4/1998 | Rosenberg et al. |
| 5,748,767 A | 5/1998 | Raab |
| 5,762,458 A | 6/1998 | Wang et al. |
| 5,767,548 A | 6/1998 | Wondrak et al. |
| 5,767,648 A | 6/1998 | Morel et al. |
| 5,767,839 A | 6/1998 | Rosenberg |
| 5,769,092 A | 6/1998 | Williamson, Jr. |
| 5,769,640 A | 6/1998 | Jacobus et al. |
| 5,776,136 A | 7/1998 | Sahay et al. |
| 5,784,542 A | 7/1998 | Ohm et al. |
| 5,789,890 A | 8/1998 | Genov et al. |
| 5,792,135 A | 8/1998 | Madhani et al. |
| 5,792,147 A | 8/1998 | Evans et al. |
| 5,806,518 A | 9/1998 | Mittelstadt |
| 5,807,377 A | 9/1998 | Madhani et al. |
| 5,815,640 A | 9/1998 | Wang et al. |
| 5,820,623 A | 10/1998 | Ng |
| 5,824,085 A | 10/1998 | Sahay et al. |
| 5,831,408 A | 11/1998 | Jacobus et al. |
| 5,841,950 A | 11/1998 | Wang et al. |
| 5,847,528 A | 12/1998 | Hui et al. |
| 5,855,553 A | 1/1999 | Tajima et al. |
| 5,855,583 A | 1/1999 | Wang et al. |
| 5,871,018 A | 2/1999 | Delp et al. |
| 5,880,976 A | 3/1999 | DiGioia, III et al. |
| 5,882,206 A | 3/1999 | Gillio |
| 5,891,157 A | 4/1999 | Day et al. |
| 5,907,487 A | 5/1999 | Rosenberg et al. |
| 5,907,664 A | 5/1999 | Wang et al. |
| 5,929,607 A | 7/1999 | Rosenberg et al. |
| 5,950,629 A | 9/1999 | Taylor et al. |
| 5,952,796 A | 9/1999 | Colgate et al. |
| 5,959,613 A | 9/1999 | Rosenberg et al. |
| 5,966,305 A | 10/1999 | Watari et al. |
| 5,971,976 A | 10/1999 | Wang et al. |
| 5,976,156 A | 11/1999 | Taylor et al. |
| 5,993,338 A | 11/1999 | Kato et al. |
| 5,995,738 A | 11/1999 | DiGioia, III et al. |
| 5,999,168 A | 12/1999 | Rosenberg et al. |
| 6,002,859 A | 12/1999 | DiGioia, III et al. |
| 6,020,876 A | 2/2000 | Rosenberg et al. |
| 6,024,576 A | 2/2000 | Bevirt et al. |
| 6,033,415 A | 3/2000 | Mittelstadt et al. |
| 6,037,927 A | 3/2000 | Rosenberg |
| 6,046,727 A | 4/2000 | Rosenberg et al. |
| 6,050,718 A | 4/2000 | Schena et al. |
| 6,063,095 A | 5/2000 | Wang et al. |
| 6,067,077 A | 5/2000 | Martin et al. |
| 6,084,587 A | 7/2000 | Tarr et al. |
| 6,097,168 A | 8/2000 | Katoh et al. |
| 6,102,850 A | 8/2000 | Wang et al. |
| 6,111,577 A | 8/2000 | Zilles et al. |
| 6,124,693 A | 9/2000 | Okanda et al. |
| 6,157,873 A | 12/2000 | DeCamp et al. |
| 6,163,124 A | 12/2000 | Ito et al. |
| 6,181,096 B1 | 1/2001 | Hashimoto et al. |
| 6,191,796 B1 | 2/2001 | Tarr |
| 6,205,411 B1 | 3/2001 | DiGioia, III et al. |
| 6,228,089 B1 | 5/2001 | Wahrburg |
| 6,233,504 B1 | 5/2001 | Das et al. |
| 6,236,875 B1 | 5/2001 | Bucholz et al. |
| 6,236,906 B1 | 5/2001 | Muller |
| 6,246,200 B1 | 6/2001 | Blumenkranz et al. |
| 6,278,902 B1 | 8/2001 | Hashimoto et al. |
| 6,281,651 B1 | 8/2001 | Haanpaa et al. |
| 6,300,937 B1 | 10/2001 | Rosenberg |
| 6,304,050 B1 | 10/2001 | Skaar et al. |
| 6,311,100 B1 | 10/2001 | Sarma et al. |
| 6,314,312 B1 | 11/2001 | Wessels et al. |
| 6,322,567 B1 | 11/2001 | Mittelstadt et al. |
| 6,325,808 B1 | 12/2001 | Bernard et al. |
| 6,329,777 B1 | 12/2001 | Itabashi et al. |

(56) References Cited

U.S. PATENT DOCUMENTS

| | | |
|---|---|---|
| 6,329,778 B1 | 12/2001 | Culp et al. |
| 6,330,837 B1 | 12/2001 | Charles et al. |
| 6,336,931 B1 | 1/2002 | Hsu et al. |
| 6,339,735 B1 | 1/2002 | Peless et al. |
| 6,341,231 B1 | 1/2002 | Ferre et al. |
| 6,342,880 B2 | 1/2002 | Rosenberg et al. |
| 6,347,240 B1 | 2/2002 | Foley et al. |
| 6,351,659 B1 | 2/2002 | Vilsmeier |
| 6,351,661 B1 | 2/2002 | Cosman |
| 6,352,532 B1 | 3/2002 | Kramer et al. |
| 6,366,272 B1 | 4/2002 | Rosenberg et al. |
| 6,368,330 B1 | 4/2002 | Hynes et al. |
| 6,369,834 B1 | 4/2002 | Zilles et al. |
| 6,377,839 B1 | 4/2002 | Kalfas et al. |
| 6,385,475 B1 | 5/2002 | Cinquin et al. |
| 6,385,508 B1 | 5/2002 | McGee et al. |
| 6,385,509 B2 | 5/2002 | Das et al. |
| 6,401,006 B1 | 6/2002 | Mizuno et al. |
| 6,405,072 B1 | 6/2002 | Cosman |
| 6,408,253 B2 | 6/2002 | Rosenberg et al. |
| 6,411,276 B1 | 6/2002 | Braun et al. |
| 6,413,264 B1 | 7/2002 | Jensen et al. |
| 6,414,711 B2 | 7/2002 | Arimatsu et al. |
| 6,417,638 B1 | 7/2002 | Guy et al. |
| 6,421,048 B1 | 7/2002 | Shih et al. |
| 6,423,077 B2 | 7/2002 | Carol et al. |
| 6,424,356 B2 | 7/2002 | Chang et al. |
| 6,428,487 B1 | 8/2002 | Burdorff et al. |
| 6,430,434 B1 | 8/2002 | Mittelstadt |
| 6,432,112 B2 | 8/2002 | Brock et al. |
| 6,434,415 B1 | 8/2002 | Foley et al. |
| 6,436,107 B1 | 8/2002 | Wang et al. |
| 6,441,577 B2 | 8/2002 | Blumenkranz et al. |
| 6,443,894 B1 | 9/2002 | Sumanaweera et al. |
| 6,450,978 B1 | 9/2002 | Brosseau et al. |
| 6,451,027 B1 | 9/2002 | Cooper et al. |
| 6,459,926 B1 | 10/2002 | Nowlin et al. |
| 6,461,372 B1 | 10/2002 | Jensen et al. |
| 6,463,360 B1 | 10/2002 | Terada et al. |
| 6,466,815 B1 | 10/2002 | Saito et al. |
| 6,468,265 B1 | 10/2002 | Evans et al. |
| 6,473,635 B1 | 10/2002 | Rasche |
| 6,486,872 B2 | 11/2002 | Rosenberg et al. |
| 6,490,467 B1 | 12/2002 | Bucholz et al. |
| 6,491,702 B2 | 12/2002 | Heilbrun et al. |
| 6,494,882 B1 | 12/2002 | Lebouitz et al. |
| 6,501,997 B1 | 12/2002 | Kakino |
| 6,507,165 B2 | 1/2003 | Kato et al. |
| 6,507,773 B2 | 1/2003 | Parker et al. |
| 6,514,082 B2 | 2/2003 | Kaufman et al. |
| 6,520,228 B1 | 2/2003 | Kennedy et al. |
| 6,522,906 B1 | 2/2003 | Salisbury, Jr. et al. |
| 6,533,737 B1 | 3/2003 | Brosseau et al. |
| 6,535,756 B1 | 3/2003 | Simon et al. |
| 6,542,770 B2 | 4/2003 | Zylka et al. |
| 6,562,055 B2 | 5/2003 | Walen |
| 6,620,174 B2 | 9/2003 | Jensen et al. |
| 6,636,161 B2 | 10/2003 | Rosenberg |
| 6,639,581 B1 | 10/2003 | Moore et al. |
| 6,665,554 B1 | 12/2003 | Charles et al. |
| 6,671,651 B2 | 12/2003 | Goodwin et al. |
| 6,676,669 B2 | 1/2004 | Charles et al. |
| 6,697,048 B2 | 2/2004 | Rosenberg et al. |
| 6,699,177 B1 | 3/2004 | Wang et al. |
| 6,702,805 B1 | 3/2004 | Stuart |
| 6,704,002 B1 | 3/2004 | Martin et al. |
| 6,704,683 B1 | 3/2004 | Hasser |
| 6,704,694 B1 | 3/2004 | Basdogan et al. |
| 6,711,432 B1 | 3/2004 | Krause et al. |
| 6,723,106 B1 | 4/2004 | Charles et al. |
| 6,728,599 B2 | 4/2004 | Wang et al. |
| 6,756,761 B2 | 6/2004 | Takahashi et al. |
| 6,757,582 B2 | 6/2004 | Brisson et al. |
| 6,778,850 B1 | 8/2004 | Adler et al. |
| 6,778,867 B1 | 8/2004 | Ziegler et al. |
| 6,781,569 B1 | 8/2004 | Gregorio et al. |
| 6,785,572 B2 | 8/2004 | Yanof et al. |
| 6,785,593 B2 | 8/2004 | Wang et al. |
| 6,788,999 B2 | 9/2004 | Green |
| 6,793,653 B2 | 9/2004 | Sanchez et al. |
| 6,799,106 B2 | 9/2004 | Fukushima et al. |
| 6,804,547 B2 | 10/2004 | Pelzer et al. |
| 6,810,314 B2 | 10/2004 | Tashiro et al. |
| 6,827,723 B2 | 12/2004 | Carson |
| 6,832,119 B2 | 12/2004 | Miller |
| 6,833,846 B2 | 12/2004 | Hasser |
| 6,837,892 B2 | 1/2005 | Shoham |
| 6,856,888 B2 | 2/2005 | Kawai |
| 6,871,117 B2 | 3/2005 | Wang et al. |
| 6,892,110 B2 | 5/2005 | Inoue et al. |
| 6,892,112 B2 | 5/2005 | Wang et al. |
| 6,892,129 B2 | 5/2005 | Miyano |
| 6,895,306 B2 | 5/2005 | Ebisawa et al. |
| 6,903,721 B2 | 6/2005 | Braun et al. |
| 6,904,823 B2 | 6/2005 | Levin et al. |
| 6,941,224 B2 | 9/2005 | Fukuyasu |
| 6,958,752 B2 | 10/2005 | Jennings, Jr. et al. |
| 6,963,792 B1 | 11/2005 | Green |
| 6,978,166 B2 | 12/2005 | Foley et al. |
| 6,982,700 B2 | 1/2006 | Rosenberg et al. |
| 6,999,852 B2 | 2/2006 | Green |
| 7,003,368 B2 | 2/2006 | Koike et al. |
| 7,006,895 B2 | 2/2006 | Green |
| 7,030,585 B2 | 4/2006 | Iwashita et al. |
| 7,034,491 B2 | 4/2006 | Kozai et al. |
| 7,035,711 B2 | 4/2006 | Watanabe et al. |
| 7,035,716 B2 | 4/2006 | Harris et al. |
| 7,038,657 B2 | 5/2006 | Rosenberg et al. |
| 7,042,175 B2 | 5/2006 | Watanabe |
| 7,044,039 B2 | 5/2006 | Powell |
| 7,047,117 B2 | 5/2006 | Akiyama et al. |
| 7,055,789 B2 | 6/2006 | Libbey et al. |
| 7,056,123 B2 | 6/2006 | Gregorio et al. |
| 7,084,596 B2 | 8/2006 | Iwashita et al. |
| 7,084,867 B1 | 8/2006 | Ho et al. |
| 7,086,056 B2 | 8/2006 | Fukushima |
| 7,087,049 B2 | 8/2006 | Nowlin et al. |
| 7,092,791 B2 | 8/2006 | Terada et al. |
| 7,097,640 B2 | 8/2006 | Wang et al. |
| 7,102,314 B2 | 9/2006 | Hayashi |
| 7,102,635 B2 | 9/2006 | Shih et al. |
| 7,103,499 B2 | 9/2006 | Goodwin et al. |
| 7,139,601 B2 | 11/2006 | Bucholz et al. |
| 7,155,316 B2 | 12/2006 | Sutherland et al. |
| 7,181,315 B2 | 2/2007 | Watanabe et al. |
| 7,193,607 B2 | 3/2007 | Moore et al. |
| 7,204,844 B2 | 4/2007 | Jensen et al. |
| 7,206,626 B2 | 4/2007 | Quaid, III |
| 7,206,627 B2 | 4/2007 | Abovitz et al. |
| 7,209,117 B2 | 4/2007 | Rosenberg et al. |
| 7,212,886 B2 | 5/2007 | Nagata et al. |
| 7,215,326 B2 | 5/2007 | Rosenberg |
| 7,221,983 B2 | 5/2007 | Watanabe et al. |
| 7,225,404 B1 | 5/2007 | Zilles et al. |
| 7,239,940 B2 | 7/2007 | Wang et al. |
| 7,245,202 B2 | 7/2007 | Levin |
| 7,249,951 B2 | 7/2007 | Bevirt et al. |
| 7,260,437 B2 | 8/2007 | Senoo et al. |
| 7,260,733 B2 | 8/2007 | Ichikawa et al. |
| 7,280,095 B2 | 10/2007 | Grant |
| 7,283,120 B2 | 10/2007 | Grant |
| 7,319,466 B1 | 1/2008 | Tarr et al. |
| 7,346,417 B2 | 3/2008 | Luth et al. |
| 7,390,325 B2 | 6/2008 | Wang et al. |
| 7,404,716 B2 | 7/2008 | Gregorio et al. |
| 7,422,582 B2 | 9/2008 | Malackowski et al. |
| 7,447,604 B2 | 11/2008 | Braun et al. |
| 7,454,268 B2 | 11/2008 | Jinno |
| 7,460,104 B2 | 12/2008 | Rosenberg |
| 7,460,105 B2 | 12/2008 | Rosenberg et al. |
| 7,466,303 B2 | 12/2008 | Yi et al. |
| 7,468,594 B2 | 12/2008 | Svensson et al. |
| 7,491,198 B2 | 2/2009 | Kockro |
| 7,542,826 B2 | 6/2009 | Hanzawa |

(56) References Cited

U.S. PATENT DOCUMENTS

| | | |
|---|---|---|
| 7,543,588 B2 | 6/2009 | Wang et al. |
| 7,573,461 B2 | 8/2009 | Rosenberg |
| 7,577,504 B2 | 8/2009 | Sawada et al. |
| 7,590,458 B2 | 9/2009 | Endo et al. |
| 7,623,944 B2 | 11/2009 | Dariush |
| 7,625,383 B2 | 12/2009 | Charles et al. |
| 7,646,161 B2 | 1/2010 | Albu-Schäffer et al. |
| 7,648,513 B2 | 1/2010 | Green et al. |
| 7,657,356 B2 | 2/2010 | Iwashita et al. |
| 7,660,623 B2 | 2/2010 | Hunter et al. |
| 7,667,687 B2 | 2/2010 | Cruz-Hernandez et al. |
| 7,683,565 B2 | 3/2010 | Quaid et al. |
| 7,714,836 B2 | 5/2010 | Rodomista et al. |
| 7,725,162 B2 | 5/2010 | Malackowski et al. |
| 7,742,801 B2 | 6/2010 | Neubauer et al. |
| 7,744,608 B2 | 6/2010 | Lee et al. |
| 7,747,311 B2 | 6/2010 | Quaid, III |
| 7,765,890 B2 | 8/2010 | Inoue et al. |
| 7,800,609 B2 | 9/2010 | Tarr et al. |
| 7,806,891 B2 | 10/2010 | Nowlin et al. |
| 7,813,368 B2 | 10/2010 | Ootaka |
| 7,813,784 B2 | 10/2010 | Marquart et al. |
| 7,813,838 B2 | 10/2010 | Sommer |
| 7,815,644 B2 | 10/2010 | Masini |
| 7,818,044 B2 | 10/2010 | Dukesherer et al. |
| 7,824,424 B2 | 11/2010 | Jensen et al. |
| 7,831,292 B2 | 11/2010 | Quaid et al. |
| 7,835,784 B2 | 11/2010 | Mire et al. |
| 7,843,158 B2 | 11/2010 | Prisco |
| 7,853,356 B2 | 12/2010 | Tsai et al. |
| 7,853,358 B2 | 12/2010 | Joly |
| 7,881,917 B2 | 2/2011 | Nagatsuka et al. |
| 7,892,243 B2 | 2/2011 | Stuart |
| 7,914,522 B2 | 3/2011 | Morley et al. |
| 7,916,121 B2 | 3/2011 | Braun et al. |
| 7,950,306 B2 | 5/2011 | Stuart |
| 7,969,288 B2 | 6/2011 | Braun et al. |
| 8,004,229 B2 | 8/2011 | Nowlin et al. |
| 8,005,571 B2 | 8/2011 | Sutherland et al. |
| 8,005,659 B2 | 8/2011 | Nelson et al. |
| 8,010,180 B2 | 8/2011 | Quaid et al. |
| 8,013,847 B2 | 9/2011 | Anastas |
| 8,049,457 B2 | 11/2011 | Okita et al. |
| 8,049,734 B2 | 11/2011 | Rosenberg et al. |
| 8,054,028 B2 | 11/2011 | Aoyama et al. |
| 8,090,475 B2 | 1/2012 | Blanc et al. |
| 8,095,200 B2 | 1/2012 | Quaid, III |
| 8,140,189 B2 | 3/2012 | Nagasaka |
| 8,155,790 B2 | 4/2012 | Oga et al. |
| 8,271,134 B2 | 9/2012 | Kato et al. |
| 8,287,522 B2 | 10/2012 | Moses et al. |
| 8,391,954 B2 | 3/2013 | Quaid, III |
| 8,405,340 B2 | 3/2013 | Moon et al. |
| 8,428,779 B2 | 4/2013 | Ohga et al. |
| 8,452,449 B2 | 5/2013 | Iida |
| 8,489,238 B2 | 7/2013 | Ooga et al. |
| 8,498,744 B2 | 7/2013 | Odermatt et al. |
| 8,541,970 B2 | 9/2013 | Nowlin et al. |
| 8,560,047 B2 | 10/2013 | Haider et al. |
| 8,644,988 B2 | 2/2014 | Prisco et al. |
| 8,740,882 B2 | 6/2014 | Jun et al. |
| 8,749,189 B2 | 6/2014 | Nowlin et al. |
| 8,749,190 B2 | 6/2014 | Nowlin et al. |
| 8,770,905 B2 | 7/2014 | Al-Mouhamed et al. |
| 8,786,241 B2 | 7/2014 | Nowlin et al. |
| 8,816,628 B2 | 8/2014 | Nowlin et al. |
| 8,823,308 B2 | 9/2014 | Nowlin et al. |
| 8,831,779 B2 | 9/2014 | Ortmaier et al. |
| 8,843,236 B2 | 9/2014 | Barajas et al. |
| 9,008,757 B2 | 4/2015 | Wu |
| 9,060,796 B2 | 6/2015 | Seo |
| 9,084,613 B2 | 7/2015 | Qutub |
| 9,119,638 B2 | 9/2015 | Schwarz et al. |
| 9,119,655 B2 | 9/2015 | Bowling et al. |
| 9,205,560 B1 | 12/2015 | Edsinger et al. |
| 9,226,796 B2 | 1/2016 | Bowling et al. |
| 9,364,291 B2 | 6/2016 | Bellettre et al. |
| 9,566,122 B2 | 2/2017 | Bowling et al. |
| 9,566,125 B2 | 2/2017 | Bowling et al. |
| 9,654,183 B2 | 5/2017 | Ma |
| 9,681,920 B2 | 6/2017 | Bowling et al. |
| 9,707,043 B2 | 7/2017 | Bozung |
| 9,795,445 B2 | 10/2017 | Bowling |
| 9,820,818 B2 | 11/2017 | Malackowski et al. |
| 10,660,711 B2 | 5/2020 | Moctezuma de la Barrera et al. |
| 11,202,682 B2 * | 12/2021 | Staunton ............... A61B 34/20 |
| 2002/0035321 A1 | 3/2002 | Bucholz et al. |
| 2003/0069591 A1 | 4/2003 | Carson et al. |
| 2003/0181934 A1 | 9/2003 | Johnston et al. |
| 2003/0208296 A1 | 11/2003 | Brisson et al. |
| 2003/0216816 A1 | 11/2003 | Ito et al. |
| 2004/0010190 A1 | 1/2004 | Shahidi |
| 2004/0024311 A1 | 2/2004 | Quaid |
| 2004/0034283 A1 | 2/2004 | Quaid |
| 2004/0034302 A1 | 2/2004 | Abovitz et al. |
| 2004/0077939 A1 | 4/2004 | Graumann |
| 2004/0106916 A1 | 6/2004 | Quaid et al. |
| 2004/0128030 A1 | 7/2004 | Nagata et al. |
| 2004/0148036 A1 | 7/2004 | Sunami |
| 2004/0157188 A1 | 8/2004 | Luth et al. |
| 2004/0243147 A1 | 12/2004 | Lipow |
| 2005/0166413 A1 | 8/2005 | Crampton |
| 2005/0171553 A1 | 8/2005 | Schwarz et al. |
| 2006/0071625 A1 | 4/2006 | Nakata et al. |
| 2006/0091842 A1 | 5/2006 | Nishiyama |
| 2006/0109266 A1 | 5/2006 | Itkowitz et al. |
| 2006/0111813 A1 | 5/2006 | Nishiyama |
| 2006/0142657 A1 | 6/2006 | Quaid et al. |
| 2006/0155262 A1 | 7/2006 | Kishi et al. |
| 2006/0176242 A1 | 8/2006 | Jaramaz et al. |
| 2006/0257379 A1 | 11/2006 | Giordano et al. |
| 2006/0258938 A1 | 11/2006 | Hoffman et al. |
| 2006/0261770 A1 | 11/2006 | Kishi et al. |
| 2006/0264742 A1 | 11/2006 | Neubauer et al. |
| 2006/0284587 A1 | 12/2006 | Teshima et al. |
| 2007/0013336 A1 | 1/2007 | Nowlin et al. |
| 2007/0085496 A1 | 4/2007 | Philipp et al. |
| 2007/0129846 A1 | 6/2007 | Birkenbach et al. |
| 2007/0142968 A1 * | 6/2007 | Prisco ............... A61B 1/00193 700/264 |
| 2007/0151389 A1 | 7/2007 | Prisco et al. |
| 2007/0156285 A1 | 7/2007 | Sillman et al. |
| 2007/0249911 A1 | 10/2007 | Simon |
| 2007/0260394 A1 | 11/2007 | Dean |
| 2007/0265527 A1 | 11/2007 | Wohlgemuth |
| 2007/0270685 A1 | 11/2007 | Kang et al. |
| 2007/0287911 A1 | 12/2007 | Haid et al. |
| 2008/0001565 A1 | 1/2008 | Nakashima et al. |
| 2008/0009697 A1 | 1/2008 | Haider et al. |
| 2008/0010706 A1 | 1/2008 | Moses et al. |
| 2008/0058776 A1 | 3/2008 | Jo et al. |
| 2008/0065111 A1 | 3/2008 | Blumenkranz et al. |
| 2008/0077158 A1 | 3/2008 | Haider et al. |
| 2008/0086029 A1 | 4/2008 | Uchiyama et al. |
| 2008/0114267 A1 | 5/2008 | Lloyd et al. |
| 2008/0161829 A1 | 7/2008 | Kang |
| 2008/0210477 A1 | 9/2008 | Takenaka et al. |
| 2008/0269602 A1 | 10/2008 | Csavoy et al. |
| 2008/0300478 A1 | 12/2008 | Zuhars et al. |
| 2009/0003975 A1 | 1/2009 | Kuduvalli et al. |
| 2009/0012532 A1 | 1/2009 | Quaid et al. |
| 2009/0037033 A1 | 2/2009 | Phillips et al. |
| 2009/0043556 A1 | 2/2009 | Axelson et al. |
| 2009/0068620 A1 | 3/2009 | Knobel et al. |
| 2009/0069942 A1 | 3/2009 | Takahashi |
| 2009/0082784 A1 | 3/2009 | Meissner et al. |
| 2009/0088774 A1 | 4/2009 | Swarup et al. |
| 2009/0088897 A1 * | 4/2009 | Zhao ............... A61B 34/30 700/250 |
| 2009/0096148 A1 | 4/2009 | Usui |
| 2009/0099680 A1 | 4/2009 | Usui |
| 2009/0102767 A1 | 4/2009 | Shiomi |
| 2009/0105878 A1 | 4/2009 | Nagasaka |
| 2009/0112316 A1 | 4/2009 | Umemoto et al. |

(56) References Cited

U.S. PATENT DOCUMENTS

| | | |
|---|---|---|
| 2009/0149867 A1 | 6/2009 | Glozman et al. |
| 2009/0209884 A1 | 8/2009 | Van Vorhis et al. |
| 2009/0245600 A1 | 10/2009 | Hoffman et al. |
| 2009/0245992 A1 | 10/2009 | Kato |
| 2009/0248038 A1 | 10/2009 | Blumenkranz et al. |
| 2009/0259412 A1 | 10/2009 | Brogardh |
| 2009/0308683 A1 | 12/2009 | Suzuki |
| 2010/0076474 A1 | 3/2010 | Yates et al. |
| 2010/0094312 A1 | 4/2010 | Ruiz Morales et al. |
| 2010/0110599 A1 | 5/2010 | Ohshima |
| 2010/0137882 A1 | 6/2010 | Quaid, III |
| 2010/0154578 A1 | 6/2010 | Duval |
| 2010/0168950 A1 | 7/2010 | Nagano |
| 2010/0174410 A1 | 7/2010 | Greer et al. |
| 2010/0286826 A1 | 11/2010 | Tsusaka et al. |
| 2010/0292707 A1 | 11/2010 | Ortmaier et al. |
| 2010/0312392 A1 | 12/2010 | Zimmermann |
| 2010/0331855 A1 | 12/2010 | Zhao et al. |
| 2010/0331859 A1 | 12/2010 | Omori |
| 2011/0015649 A1 | 1/2011 | Anvari et al. |
| 2011/0077590 A1 | 3/2011 | Plicchi et al. |
| 2011/0082468 A1 | 4/2011 | Hagag et al. |
| 2011/0082587 A1 | 4/2011 | Ziaei et al. |
| 2011/0106102 A1 | 5/2011 | Balicki et al. |
| 2011/0118751 A1 | 5/2011 | Balaji et al. |
| 2011/0130761 A1 | 6/2011 | Plaskos et al. |
| 2011/0152676 A1 | 6/2011 | Groszmann et al. |
| 2011/0160745 A1 | 6/2011 | Fielding et al. |
| 2011/0178639 A1 | 7/2011 | Kwon et al. |
| 2011/0190932 A1 | 8/2011 | Tsusaka et al. |
| 2011/0208256 A1 | 8/2011 | Zuhars |
| 2011/0257653 A1 | 10/2011 | Hughes et al. |
| 2011/0263971 A1 | 10/2011 | Nikou et al. |
| 2011/0264107 A1 | 10/2011 | Nikou et al. |
| 2011/0264112 A1 | 10/2011 | Nowlin et al. |
| 2011/0277580 A1 | 11/2011 | Cooper et al. |
| 2011/0295247 A1 | 12/2011 | Schlesinger et al. |
| 2011/0295268 A1 | 12/2011 | Roelle et al. |
| 2011/0295274 A1 | 12/2011 | Mueller |
| 2011/0295658 A1 | 12/2011 | Bastos et al. |
| 2011/0301500 A1 | 12/2011 | Maguire et al. |
| 2011/0306985 A1 | 12/2011 | Inoue et al. |
| 2012/0030429 A1 | 2/2012 | Synge |
| 2012/0059378 A1 | 3/2012 | Farrell |
| 2012/0071752 A1 | 3/2012 | Sewell et al. |
| 2012/0071893 A1 | 3/2012 | Smith et al. |
| 2012/0083922 A1 | 4/2012 | Kwak et al. |
| 2012/0120091 A1 | 5/2012 | Koudijs et al. |
| 2012/0123441 A1 | 5/2012 | Au et al. |
| 2012/0143084 A1* | 6/2012 | Shoham ................ B25J 9/1676 901/41 |
| 2012/0173021 A1 | 7/2012 | Tsusaka |
| 2012/0197182 A1 | 8/2012 | Millman et al. |
| 2012/0245595 A1 | 9/2012 | Kesavadas et al. |
| 2012/0283747 A1 | 11/2012 | Popovic |
| 2012/0323244 A1 | 12/2012 | Cheal et al. |
| 2012/0330429 A1 | 12/2012 | Axelson, Jr. et al. |
| 2013/0006267 A1* | 1/2013 | Odermatt ............... B25J 9/1628 901/41 |
| 2013/0019883 A1 | 1/2013 | Worm et al. |
| 2013/0035690 A1 | 2/2013 | Mittelstadt et al. |
| 2013/0035696 A1 | 2/2013 | Qutub |
| 2013/0060146 A1 | 3/2013 | Yang et al. |
| 2013/0060278 A1 | 3/2013 | Bozung et al. |
| 2013/0096574 A1 | 4/2013 | Kang et al. |
| 2013/0116706 A1 | 5/2013 | Lee et al. |
| 2013/0172902 A1 | 7/2013 | Lightcap et al. |
| 2013/0172905 A1 | 7/2013 | Iorgulescu et al. |
| 2013/0175969 A1* | 7/2013 | Kwon ..................... G05B 19/237 318/590 |
| 2013/0178868 A1 | 7/2013 | Roh |
| 2013/0304258 A1 | 11/2013 | Taylor et al. |
| 2013/0325029 A1 | 12/2013 | Hourtash et al. |
| 2013/0331644 A1 | 12/2013 | Pandya et al. |
| 2013/0345718 A1* | 12/2013 | Crawford ............... A61B 5/061 606/130 |
| 2014/0039517 A1 | 2/2014 | Bowling et al. |
| 2014/0039681 A1 | 2/2014 | Bowling et al. |
| 2014/0052153 A1 | 2/2014 | Griffiths et al. |
| 2014/0052154 A1 | 2/2014 | Griffiths et al. |
| 2014/0081461 A1 | 3/2014 | Williamson et al. |
| 2014/0121837 A1 | 5/2014 | Hashiguchi et al. |
| 2014/0135795 A1 | 5/2014 | Yanagihara |
| 2014/0148818 A1 | 5/2014 | Komuro et al. |
| 2014/0195205 A1 | 7/2014 | Benker et al. |
| 2014/0222023 A1 | 8/2014 | Kim et al. |
| 2014/0222207 A1 | 8/2014 | Bowling et al. |
| 2014/0275955 A1 | 9/2014 | Crawford et al. |
| 2014/0276943 A1 | 9/2014 | Bowling et al. |
| 2014/0276949 A1 | 9/2014 | Staunton et al. |
| 2014/0276952 A1 | 9/2014 | Hourtash et al. |
| 2014/0277742 A1 | 9/2014 | Wells et al. |
| 2014/0378999 A1 | 12/2014 | Crawford et al. |
| 2015/0012715 A1 | 1/2015 | Aronovich et al. |
| 2015/0032126 A1 | 1/2015 | Nowlin et al. |
| 2015/0032164 A1 | 1/2015 | Crawford et al. |
| 2015/0051733 A1 | 2/2015 | Nowlin et al. |
| 2015/0081098 A1 | 3/2015 | Kogan |
| 2015/0094736 A1 | 4/2015 | Malackowski et al. |
| 2015/0150591 A1 | 6/2015 | Takagi |
| 2015/0223941 A1 | 8/2015 | Lang |
| 2015/0289941 A1 | 10/2015 | Bowling et al. |
| 2016/0235493 A1 | 8/2016 | LeBoeuf, II et al. |
| 2016/0361070 A1 | 12/2016 | Ardel et al. |
| 2017/0024014 A1 | 1/2017 | Chizeck et al. |
| 2017/0052622 A1 | 2/2017 | Smith |
| 2017/0071680 A1 | 3/2017 | Swarup et al. |
| 2017/0128136 A1 | 5/2017 | Post |
| 2017/0143442 A1 | 5/2017 | Tesar et al. |
| 2017/0245955 A1 | 8/2017 | Bowling et al. |
| 2017/0258526 A1* | 9/2017 | Lang ........................ A61F 2/32 |
| 2017/0258532 A1* | 9/2017 | Shalayev ........... A61B 17/1626 |
| 2018/0168749 A1 | 6/2018 | Dozeman |
| 2018/0168750 A1* | 6/2018 | Staunton ................ A61B 34/76 |
| 2020/0030036 A1* | 1/2020 | Forstein ................ A61B 34/10 |
| 2020/0138518 A1* | 5/2020 | Lang ...................... A61B 5/05 |
| 2020/0281608 A1* | 9/2020 | Sharifi-Mehr ..... A61B 17/8897 |
| 2020/0297429 A1* | 9/2020 | Montane ............... A61B 50/30 |
| 2021/0068845 A1* | 3/2021 | Schers ................... A61B 34/20 |
| 2021/0353311 A1* | 11/2021 | Lavallee ............... A61B 90/11 |
| 2022/0079692 A1* | 3/2022 | Staunton ............... A61B 34/30 |
| 2022/0273396 A1* | 9/2022 | Bozung ................. A61B 34/30 |

FOREIGN PATENT DOCUMENTS

| | | | |
|---|---|---|---|
| EP | 1680007 A2 | 7/2006 | |
| EP | 1871267 A1 | 1/2008 | |
| EP | 1973487 A2 | 10/2008 | |
| EP | 2204136 A2 * | 7/2010 | ......... A61C 13/0004 |
| EP | 2666428 A1 | 11/2013 | |
| WO | 199611624 A2 | 4/1996 | |
| WO | 1999037220 A1 | 7/1999 | |
| WO | 2000021450 A1 | 4/2000 | |
| WO | 2000035366 A1 | 6/2000 | |
| WO | 2000059397 A1 | 10/2000 | |
| WO | 2000060571 A1 | 10/2000 | |
| WO | 200200131 A1 | 1/2002 | |
| WO | 2002024051 A2 | 3/2002 | |
| WO | 2002060653 A2 | 8/2002 | |
| WO | 2002065931 A1 | 8/2002 | |
| WO | 2002074500 A2 | 9/2002 | |
| WO | 2002076302 A2 | 10/2002 | |
| WO | 2003086714 A2 | 10/2003 | |
| WO | 2003094108 A2 | 11/2003 | |
| WO | 2004001569 A2 | 12/2003 | |
| WO | 2004014244 A2 | 2/2004 | |
| WO | 2004019785 A2 | 3/2004 | |
| WO | 2004069036 A2 | 8/2004 | |
| WO | 2005009215 A2 | 2/2005 | |
| WO | 2005122916 A1 | 12/2005 | |
| WO | 2006058633 A1 | 6/2006 | |
| WO | 2006063156 A1 | 6/2006 | |
| WO | 2006091494 A1 | 8/2006 | |

(56) References Cited

FOREIGN PATENT DOCUMENTS

| WO | 2007017642 A1 | 2/2007 |
|---|---|---|
| WO | 2007111749 A2 | 10/2007 |
| WO | 2007117297 A2 | 10/2007 |
| WO | 2007136739 A2 | 11/2007 |
| WO | 2007136768 A2 | 11/2007 |
| WO | 2007136769 A2 | 11/2007 |
| WO | 2007136771 A2 | 11/2007 |
| WO | 2009059330 A2 | 5/2009 |
| WO | 2010088959 A1 | 8/2010 |
| WO | 2010102384 A1 | 9/2010 |
| WO | 2011021192 A1 | 2/2011 |
| WO | 2011088541 A1 | 7/2011 |
| WO | 2011106861 A1 | 9/2011 |
| WO | 2011109041 A1 | 9/2011 |
| WO | 2011113483 A1 | 9/2011 |
| WO | 2011133873 A1 | 10/2011 |
| WO | 2011133927 A2 | 10/2011 |
| WO | 2011134083 A1 | 11/2011 |
| WO | 2011128766 A3 | 12/2011 |
| WO | 2012018816 A2 | 2/2012 |
| WO | 2012018823 A2 | 2/2012 |
| WO | 2013020026 A1 | 2/2013 |
| WO | 2013117909 A1 | 8/2013 |
| WO | 2013181507 A1 | 12/2013 |
| WO | 2013192598 A1 | 12/2013 |
| WO | 2014022786 A2 | 2/2014 |
| WO | 2014121262 A2 | 8/2014 |
| WO | 2014151550 A2 | 9/2014 |
| WO | 2015061638 A1 | 4/2015 |

OTHER PUBLICATIONS

Abovitz, R.A., Human-Interactive Medical Robotics, Abstract for CAOS 2000, 2000, pp. 71-72; 2 pages.

Ansara,. D. et al., Visual and haptic collaborative tele-presence, Computers & Graphics, 2001, pp. 789-798, vol. 25, Elsevier, Inc.; 10 pages.

Bainville, E. et al., Concepts and Methods of Registration for Computer-Integrated Surgery, Computer Assisted Orthopedic Surgery (CAOS), 1999, pp. 15-34, Hogrefe & Huber Publishers, Bern; 22 pages.

Bargar, W.L. et al., Primary and Revision Total Hip Replacement Using the Robodoc System, Clinical Orthopaedics and Related Research, Sep. 1998, pp. 82-91, No. 354; 10 pages.

Bierentzen, J. Andreas, Octree-based Volume Sculpting, Proc. Late Breaking Hot Topics, IEEE Visualization '98, pp. 9-12, 1998; 4 pages.

Bouazza-Marouf, K. et al., Robot-assisted invasive orthopaedic surgery, Mechatronics in Surgery, Jun. 1996, pp. 381-397, vol. 6, Issue 4, UK; 17 pages.

Brandt, G. et al., "CRIGOS: A Compact Robot for Image-Guided Orthopedic Surgery," Information Technology in Biomedicine, IEEE Transactions on, vol. 3, No. 4, pp. 252-260,Dec. 1999; 9 pages.

Brisson, G. et al., Precision Freehand Sculpting of Bone, Medical Image Computing and Computer-Assisted Intervention—MICCAI 2004, Lecture Notes in Computer Science, vol. 3217, Jan. 1, 2004, pp. 105-112, Springer-VerlagBerlin Heidelberg 2004; 8 pages.

Buckingham, R.O., Robotics in surgery a new generation of surgical tools incorporate computer technology and mechanical actuation to give surgeons much finer control than previously possible during some operations, IEE Review, Sep. 1994, pp. 193-196; 4pages.

Buckingham, R.O., Safe Active Robotic Devices for Surgery, Systems, Man and Cybernetics, 1993. 'Systems Engineering in the Service of Humans', Conference Proceedings., International Conference on, Oct. 17-20, 1993, pp. 355-358, vol. 5, IEEE, LeTougeut; 4 pages.

Burghart, C.R. et al., A. Pernozzoli; H. Grabowski; J. Muenchenberg; J. Albers; S. Hafeld; C. Vahl; U. Rembold; H. Woern, Robot assisted craniofacial surgery first clinical evaluation, Computer Assisted Radiology andSurgery, 1999, pp. 828-833; 7 pages.

Burghart, C.R. et al., Robot Controlled Osteotomy in Craniofacial Surgery, First International Workshop on Haptic Devices in Medical Applications Proceedings, Jun. 23, 1999, pp. 12-22, Paris, FR; 13 pages.

Burghart, C.R., Partial English Translation of Robotergestutzte Osteotomie in der craniofacialen Chirurgie (Robot Clipped Osteotomy in Craniofacial sugery), Jul. 1, 1999, GCA-Verlag, 2000, 62 pages.

Burghart, C.R., Robotergestutzte Osteotomie in der craniofacialen Chirurgie (Robot Clipped osteotomy in craniofacial surgery), Jul. 1, 1999, GCA-Verlag, 2000; 250 pages.

Catto, E., Iterative Dynamics with Temporal Coherence, Feb. 22, 2005, Menlo Park, CA, US; 24 pages.

Catto, E., Soft Constraints Reinventing the Spring, Game Developer Conference, 2011; 51 pages.

Choi, D.Y. et al., Flexure-based Manipulator for Active Handheld Microsurgical Instrument, Engineering in Medicine and Biology Society, 2005. Proceedings of the 2005 IEEE Engineering in Medicine and Biology 27th Annual Conference of theDigital Object Identifier, 2005, pp. 5085-5088, IEEE, Shanghai, China, Sep. 1-4, 2005, 4 pages.

Colgate, J.E. et al., Issues in the Haptic Display of Tool Use, Intelligent Robots and Systems 95. 'Human Robot Interaction and Cooperative Robots', Proceedings. 1995 IEEE/RSJ International Conference on, Aug. 5-9, 1995, pp. 140-145, vol. 3, IEEE, Pittsburgh, PA, USA; 6 pages.

Davies, B.L. et al., Acrobot-using robots and surgeons synergistically in knee surgery, Advanced Robotics, 1997. ICAR '97. Proceedings., 8th International Conference on, Jul. 7-9, 1997, pp. 173-178, IEEE,Monterey, CA, USA; 6 pages.

Davies, B.L. et al., Active compliance in robotic surgery-the use of force control as a dynamic constraint, Proceedings of the Institution of Mechanical Engineers, Part H: Journal of Engineeringin Medicine, Apr. 1, 1997, pp. 285-292, vol. 211, Sage, 9 pages.

Davies, B.L. et al., "Active Constraints for Robotic Knee Surgery", May 4, 2006, The Institution of Engineering and Technology, Ref. No. 2006/11372, pp. 31-48.

Davies, B.L. et al., Neurobot a special-purpose robot for neurosurgery, Robotics and Automation, 2000. Proceedings. ICRA '00. IEEE International Conference on, Apr. 2000, pp. 4103-4108, vol. 4,IEEE, San Francisco, CA, USA; 6 pages.

Davies, B.L., A review of robotics in surgery, Proceedings of the Institution of Mechanical Engineers, Part H: Journal of Engineering in Medicine Jan. 1, 2000, vol. 214, No. 1, pp. 129-140, Sage Publications; 13 pages.

Davies, B.L., Computer-assisted and robotics surgery, International Congress and Symposium Series 223, 1997, pp. 71-82, Royal Society of Medicine Press Limited; 12 pages.

Davies, B.L..., Robotics in minimally invasive surgery, Through the Keyhole: Microengineering in Minimally Invasive Surgey, IEE Colloquium on, Jun. 6, 1995, pp. 5/1-5/2, London, UK; 2 pages.

Delp, S.L. et al., Computer Assisted Knee Replacement, Clinical Orthopaedics, Sep. 1998, pp. 49-56, vol. 354, Lippincott-Raven Publishers; 8 pages.

DiGioia, A.M. et al., Computer Assisted Orthopaedic Surgery Image Guided and Robotic Assistive Technologies, Clinical Orthopaedics & Related Research:, Sep. 1998, pp. 8-16, vol. 354, Lippincott Williams & Wilkins, Pittsburgh, PA, USA; 9 pages.

Doignon, C. et all., Segmentation and guidance of multiple rigid objects for intra-operative endoscopic vision, Proceeding WDV'05/ WDV'06/ICCV'05/ECCV'06 Proceedings of the 2005/2006 International Conference on Dynamical Vision,2006, pp. 314-327, Springer-Verlag Berlin, Heidelberg, Illkirch, FR; 14 pages.

Ellis, R.E. et al., A surgical planning and guidance system for high tibial osteotomy, Computer Aided Surgery, Apr. 16, 1999, 264-274, vol. 4, Wiley-Liss, Inc.; 11 pages.

Engel, D. et al., A Safe Robot System for Craniofacial Surgery, Robotics and Automation, 2001. Proceedings 2001 ICRA. IEEE International Conference on (vol. 2), pp. 2020-2024, IEEE; 5 pages.

English language abstract and machine-assisted English translation for WO 2000/21450 A1 extracted from www.Espacenet.org on Aug. 11, 2014; 37 pages.

English language abstract and machine-assisted English translation for WO 2000/59397 A1 extracted from www.Espacenet.org on Aug. 11, 2014; 33 pages.

(56) References Cited

OTHER PUBLICATIONS

English language abstract and machine-assisted English translation for WO 2002/074500 A2 extracted from www.Espacenet.org on Aug. 11, 2014; 25 pages.
English language abstract for CN 102208835 extracted from espacenet.com database on Sep. 21, 2017, 2 pages.
English language abstract for CN 102470016 extracted from espacenet.com database on Sep. 21, 2017, 2 pages.
English language abstract for EP 1 680 007 A2 not found; however, see English language equivalent U.S. Pat. No. 7,831,292 B2 and original document extracted www.Espacenet.org on May 8, 2014; 3 pages.
English language abstract for EP 1 871 267 A1 not found; however, see English language equivalent International Publication No. WO 2006/091494 A1 and original document extracted www.Espacenet.org on May 8, 2014; 3 pages.
English language abstract for EP 1 973 487 A2 not found; equivalent WO 2007/117297 A2 and original document however, see English language extracted www.Espacenet.org on May 8, 2014; 3 pages.
English language abstract for WO 02/076302 extracted from espacenet.com database on Apr. 11, 2018, 2 pages.
English language abstract for WO 2002/065931 A1 extracted from www.espacenet.com database on Apr. 11, 2018; 2 pages.
English language abstract for WO 2004/019785 extracted from espacenet.com database on Apr. 11, 2018, 2 pages.
English language abstract for WO 2006/058633 extracted from espacenet.com database on Apr. 11, 2018, 2 pages.
Fadda, M. et al., Computer Assisted Planning for Total Knee Arthroplasty, 1997, pp. 619-628; 10 pages.
Fadda, M. et al., Computer-Assisted Knee Arthroplasty at Rizzoli Insitutes, First International Symposium on Medical Robotics and ComputerAssisted Surgery, Sep. 22-24, 1994, pp. 26-30, Pittsburgh, Pennsylvania, US; 6 pages.
Fadda, M. et al., Premiers Pas Vers La Dissectomie et la Realisation de Protheses du Genou a L'Aide de Robots, Innov. Tech. Bio. Med. , 1992, pp. 394-409, vol. 13, No. 4; 16 pages.
Fluete, M. et al., Incorporating a statistically based shape model into a system for computer-assisted anterior cruciate ligament surgery, Medical Image Analysis, Oct. 1999, pp. 209-222, vol. 3, No. 3, FR; 14 pages.
Gravel, D.P. et al., Flexible robotic assembly efforts at Ford Motor Company, Intelligent Control, 2001. (ISIC '01). Proceedings of the 2001 IEEE International Symposium on, 2001, pp. 173-182, IEEE, Detroit, Michigan, US; 10 pages.
Gravel, D.P. et al., Flexible Robotic Assembly, Measuring the Performance and Intelligence of Systems: Proceedings of the 2000 PerMIS Workshop, NIST Interagency/Internal Report (NISTIR)—970, Aug. 14-16, 2000, pp. 412-418, Sep. 1, 2001 NIST; 11pages.
Grueneis, C.O.R. et al., Clinical Introduction of the Caspar System Problems and Initial Results, 4th International Symposium of Computer Assited Orthopaedic Surgery, CAOS'99, Abstracts from CAOS '99, 1999, p. 160, Davos, Switzerland; 1 pages.
Haider, H. et al., Minimally Invasive Total Knee Arthroplasty Surgery Through Navigated Freehand Bone Cutting, Journal of Arthroplasty, Jun. 2007, vol. 22, No. 4, pp. 535-542, Elsevier B.V.; 8 pages.
Harris, S.J. et al., Experiences with Robotic Systems for Knee Surgery, CVRMed-MRCAS'97, Lecture Notes in Computer Science, 1997, pp. 757-766, vol. 1205, Springer Berlin Heidelberg,London, UK; 10 pages.
Harris, S.J. et al., Intra operative Application of a Robotic Knee Surgery System, Medical Image Computing and Computer-Assisted Intervention—MICCAl'99, 1999, pp. 1116-1124, vol. 1679, Springer-Verlag Berlin Heidelberg; 9pages.
Hassfeld, C. et al., Intraoperative Navigation Techniques Accuracy Tests and Clinical Report, In: Computer Assisted Radiology and Surgery (CARS'98), Tokyo, Jun. 1998, pp. 670-675, Elseview Science B.V.; 6 pages.
Ho, S.C. et al., Force Control for Robotic Surgery, ICAR '95, 1995, pp. 21-32, London, UK; 12 pages.
Ho, S.C. et al., Robot Assisted Knee Surgery Establishing a force control strategy incorporating active motion constraint, IEEE Engineering in Medicine and Biology, May/Jun. 1995, pp. 292-300, vol. 14, No. 3; 9 pages.
Hyosig, K. et al., Autonomous Suturing using Minimally Invasive Surgical Robots, Control Applications, Sep. 25-27, 2000. Proceedings of the 2000 IEEE International Conference on, 2000, pp. 742-747, IEEE, Anchorage, AK, USA; 6 pages.
Hyosig, K. et al., EndoBot A Robotic Assistant in Minimally Invasive Surgeries, Robotics and Automation, 2001. Proceedings 2001 ICRA. IEEE International Conference on, Seoul, KR, 2001, pp. 2031-2036, vol. 2, IEEE, Troy, NYY, USA; 6 pages.
International Search Report for Application No. PCT/US2013/053451 dated Mar. 19, 2014; 8 pages.
International Search Report for Application No. PCT/US2016/049955 dated Nov. 4, 2016, 21 pages.
International Search Report for Application No. PCT/US2014/025975 dated Sep. 26, 2014, 2 pages.
International Search Report for Application No. PCT/US2017/066071 dated Mar. 27, 2018, 4 pages.
Jakopec, M. et al., The first clinical application of a "hands-on" robotic knee surgery system, Computer Aided Surgery , 2001, pp. 329-339, vol. 6, Issue 6, Wiley-Liss, Inc.; 11 pages.
Jaramaz, B. et al., Range of Motion After Total Hip Arthroplasty Experimental Verification of the Analytical Simulator, CVRMed-MRCAS'97, Lecture Notes in Computer Science, Feb. 20, 1997, pp. 573-582, vol. 1205,Springer Berlin Heidelberg, Pittsburgh, PA, USA; 14 pages.
Kazanzides, P. et al., Architecture of a Surgical Robot, Systems, Man and Cybernetics, 1992., IEEE International Conference on, Oct. 18-21, 1992, pp. 1624-1629, vol. 2, IEEE,Chicago, IL, USA; 6 pages.
Khadem, R. et al., Comparative Tracking Error Analysis of Five Different Optical Tracking Systems, Computer Aided Surgery, 2000, pp. 98-107, vol. 5, Stanford, CA,USA; 10 pages.
Kienzle, III, T.C. et al., An Integrated CAD-Robotics System for Total Knee Replacement Surgery, Systems, Man and Cybernetics, 1992., IEEE International Conference on, Oct. 18-21, 1992, pp. 1609-1614, vol. 2,IEEE, Chicago, IL, USA; 6 pages.
Kienzle, III, T.C. et al., Total Knee Replacement Computer-assisted surgical system uses a calibrated robot, Engineering in Medicine and Biology, May 1995, pp. 301-306, vol. 14, Issue 3,IEEE; 35 pages.
Korb, W. et al., Development and First Patient Trial of a Surgical Robot for Complex Trajectory Milling, Computer Aided Surgery, 2003, vol. 8, pp. 247-256, CAS Journal LLC; 10 pages.
Koseki, Y. et al., Robotic assist for MR-guided surgery using leverage and parallelepiped mechanism, Medical Image Computing and Computer-Assisted Intervention—MICCAI 2000, Lecture Notes in Computer Science, 2000, pp. 940-948, vol. 1935, Springer Berlin Heidelberg; 9 pages.
Kozlowski, D. et al., Automated Force Controlled Assembly Utilizing a Novel Hexapod Robot Manipulator, Automation Congress,2002 Proceedings of the 5th Biannual World, 2002, pp. 547-552, vol. 14, IEEE; 6 pages.
Lavallee, S. et al., Computer Assisted Spine Surgery a technique for accurate transpedicular screw fixation using CT data and a 3-D optical localizer, Journal of Image Guided Surgery, 1995, pp. 65-73; 9 pages.
Lea, J.T. et al., Registration and immobilization in robot-assisted surgery, Journal of Image Guided Surgery, Computer Aided Surgery, 1995, vol. 1, No. 2, pp. 80-87; 11 pages.
Lea, J.T. Registration Graphs a Language for Modeling and Analyzing Registration in Image-Guided Surgery, Dec. 1998, Evanston, Illinois, US; 49 pages.
Leitner, F. et al., Computer-Assisted Knee Surgical Total Replacement, CVRMed-MRCAS'97, Lecture Notes in Computer Science vol. 1205, 1997, pp. 629-638, Springer Berlin Heidelberg, Jan. 1, 1997; 10 pages.
Lembcke, S., Realtime Rigid Body Simulation Using Impulses, 2006, Morris, MN, US; 5 pages.

(56) References Cited

OTHER PUBLICATIONS

Levison, T.J. et al., Surgical Navigation for THR a Report on Clinical Trial Utilizing HipNav, MICCAI 2000, LNCS 1935, pp. 1185-1187, 2000, Springer-Verlag Berlin Heidelberg; 3 pages.
Louhisalmi, Y. et al., Development of a Robotic Surgical Assistant, 1994, pp. 1043-1044, IEEE, Linnanmaa, Oulu, FI; 2 pages.
Matsen, F.A. et al., Robotic Assistance in Orthopaedic Surgery a Proof of Principle Using Distal Femoral Arthroplasty, Clinical Orthopaedic Related Research, Nov. 1993, pp. 178-186, vol. 296; 9 pages.
Meng, C. et al., Remote surgery case robot-assisted teleneurosurgery, Robotics and Automation, 2004. Proceedings. ICRA '04. 2004 IEEE International Conference on, Apr. 26-May 1, 2004, pp. 819-823, vol. 1, IEEE, New Orleans, LA, USA; 5 pages.
Moctezuma, J.L.. et al., A Computer and Robotic Aided Surgery System for Accomplishing Osteotomies, First International Symposium on Medical Robotics and Computer Assisted Surgery, Sep. 22-24, 1994, Pittsburgh, Pennsylvania, US; 6 pages.
Nolte, L.P. et al., A Novel Approach to Computer Assisted Spine Surgery, Proc. First International Symposium on Medical Robotics and Computer Assisted Surgery, Pittsburgh, 1994, pp. 323-328; 7 pages.
O'Toole, R.V. et al., Biomechanics for Preoperative Planning and Surgical Simulations in Orthopaedics, Computers in Biology and Medicine, Mar. 1995, pp. 183-191, vol. 25, Issue 2; 8 pages.
Orto Maquet and Caspar: An Automated Cell for Prosthesis Surgery, Robotics World, Sep./Oct. 1999, pp. 30-31, Circular No. 87 on Reader Reply Card; 2 pages.
Paul, H.A. et al., A Surgical Robot for Total Hip Replacement Surgery, International Conference on Robotics and Automation, 1992, pp. 606-611, IEEE, Nice, FR; 6 pages.
Paul, H.A. et al., Development of a Surgical Robot for Cementless Total Hip Anthroplasty, Clinical Orthopaedics and Related Research, Dec. 1992, pp. 57-66, No. 285, Sacramento, CA, USA; 10 pages.
Paul, H.A. et al., Robotic Execution of a Surgical Plan, Systems, Man and Cybernetics, 1992., IEEE International Conference on, Oct. 18-21, 1992,pp. 1621-1623, IEEE, Sacramento, California, US; 3 pages.
Preising, B. et al., A Literature Review Robots in Medicine, Engineering in Medicine and Biology Magazine, IEEE (vol. 10, Issue: 2), Jun. 1991, pp. 13-22, IEEE; 10 pages.
Quaid, A.E. et al., Haptic Information Displays for Computer-Assisted Surgery, Robotics and Automation, 2002 Proceedings. ICRA '02. IEEE International Conference on, May 2002, pp. 2092-2097, vol. 2, IEEE, Washington DC, USA; 6 pages.
Raczkowsky, J. et al., Ein Robotersystem fur craniomaxillofaciale chirurgische Eingriffe (A robotic system for surgical procedures craniomaxillofaciale), with English language abstract, Computer Forsch. Entw., 1999, pp. 24-35, vol. 14,Springer-Verlag; 12 pages.
Rembold, U. et al., Surgical Robotics: An Introduction, Journal of Intelligent and Robotic Systems vol. 30, No. 1, pp. 1-28, 2001, Kluwer Academic Publishers; 28 pages.
Riviere, C.N. et al., Modeling and Canceling Tremor in Human-Machine Interfaces, Engineering in Medicine and Biology Magazine, IEEE, vol. 15, Issue 3, May/Jun. 1996, p. 29-36, IEEE; 8 pages.
Rohling, R. et al., Comparison of Relative Accuracy Between a Mechanical and an Optical Position Tracker for Image-Guided Neurosurgery, Journal of Image Guided Surgery, 1995, pp. 30-34, vol. 1, No. 1; 4 pages.
Salisbury, J.K., Active Stiffness Control of a Manipulator in Cartesian Coordinates, Decision and Control including the Symposium on Adaptive Processes, 1980 19th IEEE Conference on, Dec. 1980, pp. 95-100, vol. 19, IEEE, Stanford, CA, USA; 7 pages.
Santos-Munne, Julio J. et al., A Stereotactic/Robotic System for Pedicle Screw Placement, Interactive Technology and the New Paradigm for Healthcare, (Proceedings of theMedicine Meets Virtual Reality III Conference, San Diego, 1995), pp. 326-333, IOS Press and Ohmsha, 8 pages.
Satava, R.M., History of Robotic Surgery the early chronicles a personal historical perspective, Surgical Laparoscopic Endoscopic Percutaneous Technology, Feb. 2002, vol. 12 pp. 6-16, WebSurg, 6 pages.
Schmidt, T. et al., EasyGuide Neuro, A New System for Image-Guided Planning, Simulation and Navigation in Neurosurgery, Biomedical Engineering, vol. 40, Supplement 1, 1995, pp. 233-234, Hamburg, DE; 2 pages, and partial English language translation of EasyGuide Neuro, A New System for Image-Guided Planning, Simulation and Navigation in Neurosurgery, 1 page.
Shinsuk, P., Safety Strategies for Human-Robot Interaction in Surgical Environment, SICE-ICASE, 2006. International Joint Conference, Oct. 18-21, 2006, pp. 1769-1773, IEEE, Bexco, Busan, SK; 5 pages.
Siebert, W. et al., Technique and first clinical results of robot-assisted total knee replacement, The Knee, Sep. 2002, pp. 173-180, vol. 9, Issue 3, Elsevier B.V.; 8 pages.
Siebold, U. et al., Prototype of Instrument for Minimally Invasive Surgery with 6-Axis Force Sensing Capability, Robotics and Automation, 2005. ICRA 2005. Proceedings of the 2005 IEEE International Conference on, Apr. 18-22, 2005, pp. 498-503, IEEE, Barcelona, Spain; 6 pages.
Sim, C. et al., Image-Guided Manipulator Compliant Surgical Planning Methodology for Robotic Skull-Base Surgery, Medical Imaging and Augmented Reality, 2001. Proceedings. International Workshop on, Jun. 10-12, 2001, pp. 26-29, EEE, Shatin, HK; 4 pages.
Simon, D.A. et al., Accuracy validation in image-guided orthopaedic surgery, In Medical Robotics and Computer Assisted Surgery, 1995, pp. 185-192, Wiley; 8 pages.
Spencer, E.H., The ROBODOC Clinical Trial A Robotic Assistant for Total Hip Arthroplasty, Orthopaedic Nursing, Jan.-Feb. 1996, pp. 9-14, vol. 15, Issue 1; 6 pages.
Spetzger, U. et al., Frameless Neuronavigation in Modern Neurosurgery, Minimally Invasive Neurosurgery, Dec. 1995, pp. 163-166, vol. 38; 4 pages.
Taylor, R. et al., A Steady-Hand Robotic System for Microsurgical Augementation, MICCA199: the Second International Conference on Medical ImageComputing and Computer-Assisted Intervention, Cambridge, England, Sep. 19-22, 1999. MICCAI99 Submission #1361999, pp. 1031-1041, Springer-Verlag Berlin Heidelberg, 11 pages.
Taylor, R.H. et al., A Model-Based Optimal Planning and Execution System with Active Sensing and Passive Manipulation for Augmentation of HumanPrecision in Computer-Integrated Surgery, Section 4 Robotic Systems and Task-Level Programming, Experimental Robotics II, The 2nd International Symposium, Lecture Notes in Control and Information Sciences, pp. 177-195, vol. 190, Springer BerlinHeidelberg, Toulouse, FR, Jun. 25-27, 1991; 19 pages.
Taylor, R.H. et al., An Image-directed Robotic System for Hip Replacement Surgery, Oct. 1990, pp. 111-116, vol. 8, No. 5; 7 pages.
Taylor, R.H. et al., An Image-Directed Robotic System for Precise Orthopaedic Surgery, Robotics and Automation, IEEE Transactions on, Jun. 1994, pp. 261-275, vol. 10, Issue 3, IEEE; 15 pages.
Tonet, O. et al., An Augmented Reality Navigation System for Computer Assisted Arthroscopic Surgery of the Knee, Medical Image Computing and Computer-AssistedIntervention—MICCAI 2000, Lecture Notes in Computer Science, 2000, pp. 1158-1162, vol. 1935, Springer Berlin Heidelberg; 5 pages.
Troccaz, J. et al., A passive arm with dynamic constraints a solution to safety problems in medical robotics, Systems, Man and Cybernetics, 1993. 'Systems Engineering in the Service of Humans', Conference Proceedings., InternationalConference on, Oct. 17-20, 1993, pp. 166-171, vol. 3, IEEE, Le Touquet, FR; 6 pages.
Troccaz, J. et al., Semi-Active Guiding Systems in Surgery. A Two-DOF Prototype of the Passive Arm with Dynamic Constraints (PADyC), Mechatronics, Jun. 1996, pp. 399-421, vol. 6, Issue 4, 1996, Elsevier Ltd., UK; 23 pages.
Troccaz, J. et al., Guiding systems for computer-assisted surgery introducing synergistic devices and discussing the different approaches, Medical Image Analysis, Jun. 1998, vol. 2, No. 2, pp. 101-119, Elsevier B.V.; 19 pages.

(56) References Cited

OTHER PUBLICATIONS

Van Ham, G. et al., Accuracy study on the registration of the tibia by means of an intramedullary rod in robot-assisted total knee arthroplasty, PosterSession-Knee Arthroplasty—Valencia Foyer, 46th Annual Meeting, Orthopaedic Research Society, Mar. 12-15, 2000, Orlando, Florida, Jan. 1, 2010, p. 450; 1 pages.

Van Ham, G. et al., Machining and Accuracy Studies for a Tibial Knee Implant Using a Force-Controlled Robot, Computer Aided Surgery, Feb. 1998, pp. 123-133, vol. 3, Wiley-Liss, Inc., Heverlee BE; 11 pages.

Want, T. et al., A robotized surgeon assistant, Intelligent Robots and Systems '94. 'Advanced Robotic Systems and the Real World', IROS '94. Proceedings of the IEEE/RSJ/GI International Conference on,Sep. 12-16, 1994, pp. 862-869, vol. 2, IEEE, Munich, Germany; 8 pages.

Watanable, E. et al., Three-Dimensional Digitizer (Neuronavigator); New Equipment for Computed Tomography-Guided Stereotaxic Surgery, Surgical Neurology, Jun. 1987, pp. 543-547, vol. 27, Issue 6, ElsevierInc.; 5 pages.

Yoshimine, Kato A. et al., A frameless, armless navigational system for computer-assisted neurosurgery. Technical note, Journal of Neurosurgery, vol. 74, May 1991, pp. 845-849; 5 pages.

Zilles, C.B. et al., A Constraint-Based God-object Method for Haptic Display, Intelligent Robots and Systems 95. 'Human Robot Interaction and Cooperative Robots', Proceedings. 1995 IEEE/RSJ International Conference on , Aug. 5-9-, 1995, pp. 146-151, vol. 3, IEEE, MIT, Cambridge, MA, USA; 6 pages.

\* cited by examiner

TECHNIQUES FOR MODIFYING TOOL OPERATION IN A SURGICAL ROBOTIC SYSTEM BASED ON COMPARING ACTUAL AND COMMANDED STATES OF THE TOOL RELATIVE TO A SURGICAL SITE

CROSS-REFERENCE TO RELATED APPLICATIONS

The subject application is a continuation of U.S. Nonprovisional patent application Ser. No. 15/840,278, filed Dec. 13, 2017, which claims priority to and all the benefits of U.S. Provisional Pat. App. No. 62/435,254, filed on Dec. 16, 2016, the contents of each of the aforementioned applications being hereby incorporated by reference in their entirety.

TECHNICAL FIELD

The disclosure relates generally to techniques for modifying tool operation based on comparing actual and commanded states of the tool relative to a surgical site.

BACKGROUND

Robotic systems are commonly used to perform surgical procedures and typically include a robot comprising a robotic arm and an end effector coupled to an end of the robotic arm. The robotic system commands the end effector along a cutting path for engaging a surgical site. Often, a supplemental tracking system, such as optical localization, is utilized to track positioning of the robot and the surgical site. Kinematic data from the robot may be aggregated with supplemental data from the tracking system to update positioning of the robot along the commanded cutting path. Such aggregation is used to provide redundancy for the critical task of positioning the end effector and to improve accuracy by accounting for kinematic errors such as residual kinematic calibration error and link deflection.

Tracking systems often track the robot and the anatomy at the surgical site at much higher frequencies than the closed loop bandwidth of the robot's response. Tracking systems can respond in near-real time, whereas the robot arm is limited by inertia and available power. Moreover, anatomy movement can be faster than the robot can respond. As a result, updating positioning of the robot based on data from the tracking system is a delayed process. This delay helps to avoid undesirable effects, such as positive feedback.

Failure to account for the lag necessary to prevent positive feedback, the near real-time actual positions of the end effector, and fast movements of the anatomy cause cutting inaccuracies at the surgical site. The issue is worsened when subsequent commanded cutting paths are generated based on previous commanded cutting paths, wherein neither the previous nor the subsequent commanded cutting path account for the near real-time, actual positions of the end effector, thereby causing regenerative cutting errors.

As such, there is a need in the art for systems and methods for addressing at least the aforementioned problems.

SUMMARY

According to a first aspect, a method is provided for operating a robotic surgical system, the robotic surgical system comprising a surgical tool including a tool center point (TCP) and the surgical tool being configured to manipulate a target bone, a manipulator comprising a plurality of links and being configured to support the surgical tool, a navigation system comprising a localizer configured to monitor states of the manipulator and the target bone, and one or more controllers coupled to the manipulator and the navigation system, and with the method comprising the one or more controllers performing the steps of: determining, using data from one or more of the manipulator and the navigation system, commanded states of the TCP for moving the surgical tool along a cutting path relative to the target bone for removing material from the target bone in preparation for an implant; determining, using the data from one or more of the manipulator and the navigation system, actual states of the TCP responsive to commanded movement of the surgical tool along the cutting path relative to the target bone, wherein each one of the commanded states of the TCP has a corresponding one of the actual states of the TCP for a given time step; comparing the corresponding commanded and actual states of the TCP for one or more given time steps for determining a deviation between the corresponding commanded and actual states; and based on an outcome of comparing the corresponding commanded and actual states of the TCP, modifying operation of the surgical tool to account for the deviation.

According to a second aspect, a robotic surgical system is provided that comprises: a surgical tool including a tool center point (TCP) and being configured to manipulate a target bone; a manipulator comprising a plurality of links and being configured to support the surgical tool; a navigation system comprising a localizer being configured to monitor states of the manipulator and the target bone; and one or more controllers coupled to the manipulator and the navigation system and being configured to: determine, using data from one or more of the manipulator and the navigation system, commanded states of the TCP to move the surgical tool along a cutting path relative to the target bone to remove material from the target bone in preparation for an implant; determine, using the data from one or more of the manipulator and the navigation system, actual states of the TCP responsive to commanded movement of the surgical tool along the cutting path relative to the target bone, wherein each one of the commanded states of the TCP has a corresponding one of the actual states of the TCP for a given time step; compare the corresponding commanded and actual states of the TCP for one or more given time steps to determine a deviation between the corresponding commanded and actual states; and based on an outcome of comparing the corresponding commanded and actual states of the TCP, modify operation of the surgical tool to account for the deviation.

The system and method determine near real-time, actual states of the surgical tool and/or tracker along the first path independent of the delay of the first filter. The system and method advantageously exploit raw or lightly (second) filtered raw kinematic measurement data and/or navigation data to modify operation of the surgical tool. Since the second filtered kinematic measurement data and/or navigation data is near instantaneous, the actual states of the surgical tool can be determined in near real time and faster than using the commanded (first filtered) states alone. The system and method acquire and utilize actual states of the surgical tool and/or tracker, which are faster than the delayed commanded states. Consequently, the actual and commanded states are compared to properly account for deviations. By doing so, the system and method increase path or cutting accuracy at the surgical site and reduce the possibility for regenerative cutting errors. The system and method may exhibit advantages other than those described herein.

BRIEF DESCRIPTION OF THE DRAWINGS

Advantages of the present invention will be readily appreciated as the same becomes better understood by reference to the following detailed description when considered in connection with the accompanying drawings wherein.

DETAILED DESCRIPTION

I. Overview

Referring to the Figures, wherein like numerals indicate like or corresponding parts throughout the several views, a robotic surgical system 10 (hereinafter "system") and method for operating the system 10 are shown throughout.

Figure 1:
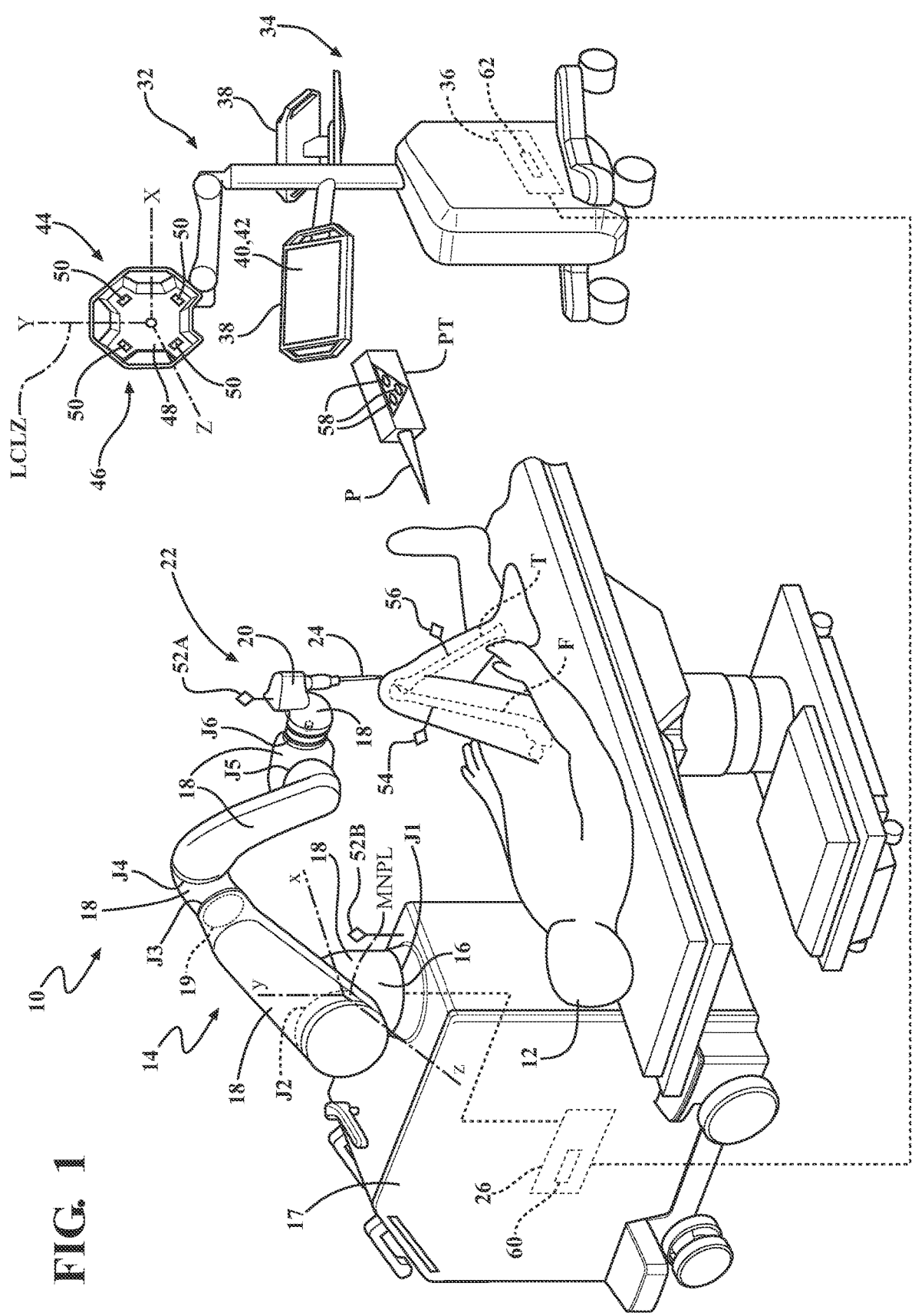
FIG. 1 is a perspective view of a robotic surgical system for manipulating a target tissue of a patient with a tool, according to one embodiment.

As shown in FIG. 1, the system 10 is a robotic surgical system for treating an anatomy (surgical site) of a patient 12, such as bone or soft tissue. In FIG. 1, the patient 12 is undergoing a surgical procedure. The anatomy in FIG. 1 includes a femur (F) and a tibia (T) of the patient 12. The surgical procedure may involve tissue removal or treatment. Treatment may include cutting, coagulating, lesioning the tissue, treatment in place of tissue, or the like. In some embodiments, the surgical procedure involves partial or total knee or hip replacement surgery. In one embodiment, the system 10 is designed to cut away material to be replaced by surgical implants, such as hip and knee implants, including unicompartmental, bicompartmental, multicompartmental, or total knee implants. Some of these types of implants are shown in U.S. Patent Application Publication No. 2012/ 0330429, entitled, "Prosthetic Implant and Method of Implantation," the disclosure of which is hereby incorporated by reference. Those skilled in the art appreciate that the system 10 and method disclosed herein may be used to perform other procedures, surgical or non-surgical, or may be used in industrial applications or other applications where robotic systems are utilized.

The system 10 includes a manipulator 14. The manipulator 14 has a base 16 and plurality of links 18. A manipulator cart 17 supports the manipulator 14 such that the manipulator 14 is fixed to the manipulator cart 17. The links 18 collectively form one or more arms of the manipulator 14. The manipulator 14 may have a serial arm configuration (as shown in FIG. 1) or a parallel arm configuration. In other embodiments, more than one manipulator 14 may be utilized in a multiple arm configuration. The manipulator 14 comprises a plurality of joints (J) and a plurality of joint encoders 19 located at the joints (J) for determining position data of the joints (J). For simplicity, only one joint encoder 19 is illustrated in FIG. 1, although it is to be appreciated that the other joint encoders 19 may be similarly illustrated. The manipulator 14 according to one embodiment has six joints (J1-J6) implementing at least six-degrees of freedom (DOF) for the manipulator 14. However, the manipulator 14 may have any number of degrees of freedom and may have any suitable number of joints (J) and redundant joints (J).

The base 16 of the manipulator 14 is generally a portion of the manipulator 14 that is stationary during usage thereby providing a fixed reference coordinate system (i.e., a virtual zero pose) for other components of the manipulator 14 or the system 10 in general. Generally, the origin of a manipulator coordinate system MNPL is defined at the fixed reference of the base 16. The base 16 may be defined with respect to any suitable portion of the manipulator 14, such as one or more of the links 18. Alternatively, or additionally, the base 16 may be defined with respect to the manipulator cart 17, such as where the manipulator 14 is physically attached to the cart 17. In a preferred embodiment, the base 16 is defined at an intersection of the axes of joints J1 and J2 (see FIG. 3). Thus, although joints J1 and J2 are moving components in reality, the intersection of the axes of joints J1 and J2 is nevertheless a virtual fixed reference point, which does not move in the manipulator coordinate system MNPL. The manipulator 14 and/or manipulator cart 17 house a manipulator computer 26, or other type of control unit.

A surgical tool 20 (hereinafter "tool") couples to the manipulator 14 and is movable relative to the base 16 to interact with the anatomy in certain modes. The tool 20 is or forms part of an end effector 22 in certain modes. The tool 20 may be grasped by the operator. One exemplary arrangement of the manipulator 14 and the tool 20 is described in U.S. Pat. No. 9,119,655, entitled, "Surgical Manipulator Capable of Controlling a Surgical Instrument in Multiple Modes," the disclosure of which is hereby incorporated by reference. The manipulator 14 and the tool 20 may be arranged in alternative configurations. The tool 20 can be like that shown in U.S. Patent Application Publication No. 2014/0276949, filed on Mar. 15, 2014, entitled, "End Effector of a Surgical Robotic Manipulator," hereby incorporated by reference.

The tool 20 includes an energy applicator 24 designed to contact the tissue of the patient 12 at the surgical site. The energy applicator 24 may be a drill, a saw blade, a bur, an ultrasonic vibrating tip, or the like. The tool 20 comprises a TCP, which in one embodiment, is a predetermined reference point defined at the energy applicator 24. The TCP has known position in its own coordinate system. In one embodiment, the TCP is assumed to be located at the center of a spherical of the tool 20 such that only one point is tracked. The TCP may relate to a bur having a specified diameter. The TCP may be defined according to various manners depending on the configuration of the energy applicator 24.

Figure 2:
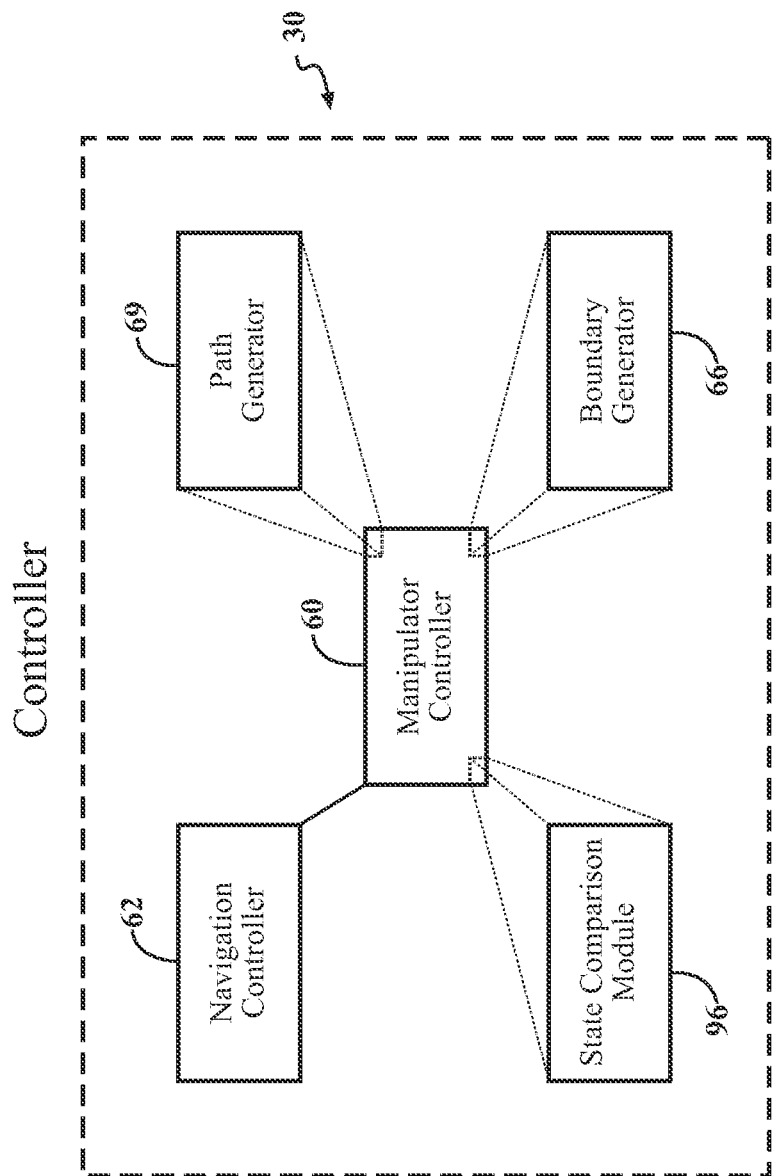
FIG. 2 is a block diagram of a controller for controlling the robotic surgical system, according to one embodiment.

Referring to FIG. 2, the system 10 includes a controller 30. The controller 30 includes software and/or hardware for controlling the manipulator 14. The controller 30 directs the motion of the manipulator 14 and controls a state (position and/or orientation) of the tool 20 with respect to a coordinate system. In one embodiment, the coordinate system is the manipulator coordinate system MNPL, as shown in FIG. 1. The manipulator coordinate system MNPL has an origin located at any suitable pose with respect to the manipulator 14. Axes of the manipulator coordinate system MNPL may be arbitrarily chosen as well. Generally, the origin of the manipulator coordinate system MNPL is defined at the fixed reference point of the base 16. One example of the manipulator coordinate system MNPL is described in U.S. Pat. No. 9,119,655, entitled, "Surgical Manipulator Capable of Controlling a Surgical Instrument in Multiple Modes," the disclosure of which is hereby incorporated by reference.

As shown in FIG. 1, the system 10 further includes a navigation system 32. One example of the navigation system 32 is described in U.S. Pat. No. 9,008,757, filed on Sep. 24, 2013, entitled, "Navigation System Including Optical and Non-Optical Sensors," hereby incorporated by reference. The navigation system 32 is configured to track movement of various objects. Such objects include, for example, the manipulator 14, the tool 20 and the anatomy, e.g., femur F and tibia T. The navigation system 32 tracks these objects to gather state information of each object with respect to a (navigation) localizer coordinate system LCLZ. Coordinates in the localizer coordinate system LCLZ may be transformed to the manipulator coordinate system MNPL, and/or vice-versa, using transformation techniques described herein.

The navigation system 32 includes a cart assembly 34 that houses a navigation computer 36, and/or other types of control units. A navigation interface is in operative communication with the navigation computer 36. The navigation interface includes one or more displays 38. The navigation system 32 is capable of displaying a graphical representation of the relative states of the tracked objects to the operator using the one or more displays 38. First and second input devices 40, 42 may be used to input information into the navigation computer 36 or otherwise to select/control certain aspects of the navigation computer 36. As shown in FIG. 1, such input devices 40, 42 include interactive touchscreen displays. However, the input devices 40, 42 may include any one or more of a keyboard, a mouse, a microphone (voice-activation), gesture control devices, and the like. The controller 30 may be implemented on any suitable device or devices in the system 10, including, but not limited to, the manipulator computer 26, the navigation computer 36, and any combination thereof.

The navigation system 32 also includes a navigation localizer 44 (hereinafter "localizer") coupled to the navigation computer 36. In one embodiment, the localizer 44 is an optical localizer and includes a camera unit 46. The camera unit 46 has an outer casing 48 that houses one or more optical sensors 50.

The navigation system 32 includes one or more trackers. In one embodiment, the trackers include a pointer tracker PT, one or more manipulator trackers 52, a first patient tracker 54, and a second patient tracker 56. In the illustrated embodiment of FIG. 1, the manipulator tracker 52 is firmly attached to the tool 20 (i.e., tracker 52A), the first patient tracker 54 is firmly affixed to the femur F of the patient 12, and the second patient tracker 56 is firmly affixed to the tibia T of the patient 12. In this embodiment, the patient trackers 54, 56 are firmly affixed to sections of bone. The pointer tracker PT is firmly affixed to a pointer P used for registering the anatomy to the localizer coordinate system LCLZ. The manipulator tracker 52 may be affixed to any suitable component of the manipulator 14, in addition to, or other than the tool 20, such as the base 16 (i.e., tracker 52B), or any one or more links 18 of the manipulator 14. Those skilled in the art appreciate that the trackers 52, 54, 56, PT may be fixed to their respective components in any suitable manner.

Any one or more of the trackers may include active markers 58. The active markers 58 may include light emitting diodes (LEDs). Alternatively, the trackers 52, 54, 56 may have passive markers, such as reflectors, which reflect light emitted from the camera unit 46. Other suitable markers not specifically described herein may be utilized.

The localizer 44 tracks the trackers 52, 54, 56 to determine a state of each of the trackers 52, 54, 56, which correspond respectively to the state of the object respectively attached thereto. The localizer 44 provides the state of the trackers 52, 54, 56 to the navigation computer 36. In one embodiment, the navigation computer 36 determines and communicates the state the trackers 52, 54, 56 to the manipulator computer 26. As used herein, the state of an object includes, but is not limited to, data that defines the position and/or orientation of the tracked object or equivalents/derivatives of the position and/or orientation. For example, the state may be a pose of the object, and may include linear data, and/or angular velocity data, and the like.

Although one embodiment of the navigation system 32 is shown in the Figures, the navigation system 32 may have any other suitable configuration for tracking the manipulator 14 and the patient 12. In one embodiment, the navigation system 32 and/or localizer 44 are ultrasound-based. For example, the navigation system 32 may comprise an ultrasound imaging device coupled to the navigation computer 36. The ultrasound imaging device images any of the aforementioned objects, e.g., the manipulator 14 and the patient 12, and generates state signals to the controller 30 based on the ultrasound images. The ultrasound images may be 2-D, 3-D, or a combination of both. The navigation computer 36 may process the images in near real-time to determine states of the objects. The ultrasound imaging device may have any suitable configuration and may be different than the camera unit 46 as shown in FIG. 1.

In another embodiment, the navigation system 32 and/or localizer 44 are radio frequency (RF)-based. For example, the navigation system 32 may comprise an RF transceiver coupled to the navigation computer 36. The manipulator 14 and the patient 12 may comprise RF emitters or transponders attached thereto. The RF emitters or transponders may be passive or actively energized. The RF transceiver transmits an RF tracking signal and generates state signals to the controller 30 based on RF signals received from the RF emitters. The navigation computer 36 and/or the controller 30 may analyze the received RF signals to associate relative states thereto. The RF signals may be of any suitable frequency. The RF transceiver may be positioned at any suitable location to track the objects using RF signals effectively. Furthermore, the RF emitters or transponders may have any suitable structural configuration that may be much different than the trackers 52, 54, 56 as shown in FIG. 1.

In yet another embodiment, the navigation system 32 and/or localizer 44 are electromagnetically based. For example, the navigation system 32 may comprise an EM transceiver coupled to the navigation computer 36. The manipulator 14 and the patient 12 may comprise EM components attached thereto, such as any suitable magnetic tracker, electro-magnetic tracker, inductive tracker, or the like. The trackers may be passive or actively energized. The EM transceiver generates an EM field and generates state signals to the controller 30 based upon EM signals received from the trackers. The navigation computer 36 and/or the controller 30 may analyze the received EM signals to associate relative states thereto. Again, such navigation system 32 embodiments may have structural configurations that are different than the navigation system 32 configuration as shown throughout the Figures.

Those skilled in the art appreciate that the navigation system 32 and/or localizer 44 may have any other suitable components or structure not specifically recited herein. Furthermore, any of the techniques, methods, and/or components described above with respect to the camera-based navigation system 32 shown throughout the Figures may be implemented or provided for any of the other embodiments of the navigation system 32 described herein. For example, the navigation system 32 may utilize solely inertial tracking or any combination of tracking techniques.

As shown in FIG. 2, the controller 30 further includes software modules. The software modules may be part of a computer program or programs that operate on the manipulator computer 26, navigation computer 36, or a combination thereof, to process data to assist with control of the system 10. The software modules include instructions stored in memory on the manipulator computer 26, navigation computer 36, or a combination thereof, to be executed by one or more processors of the computers 26, 36. Additionally, software modules for prompting and/or communicating with the operator may form part of the program or programs and may include instructions stored in memory on the manipulator computer 26, navigation computer 36, or a combination thereof. The operator interacts with the first and second input devices 40, 42 and the one or more displays 38 to communicate with the software modules. The user interface software may run on a separate device from the manipulator computer 26 and navigation computer 36.

The controller 30 includes a manipulator controller 60 for processing data to direct motion of the manipulator 14. In one embodiment, as shown in FIG. 1, the manipulator controller is implemented on the manipulator computer 26. The manipulator controller 60 may receive and process data from a single source or multiple sources. The controller 30 further includes a navigation controller 62 for communicating the state data relating to the femur F, tibia T, and manipulator 14 to the manipulator controller 60. The manipulator controller 60 receives and processes the state data provided by the navigation controller 62 to direct movement of the manipulator 14. In one embodiment, as shown in FIG. 1, the navigation controller 62 is implemented on the navigation computer 36. The manipulator controller 60 or navigation controller 62 may also communicate states of the patient 12 and manipulator 14 to the operator by displaying an image of the femur F and/or tibia T and the manipulator 14 on the one or more displays 38. The manipulator computer 26 or navigation computer 36 may also command display of instructions or request information using the display 38 to interact with the operator and for directing the manipulator 14.

Figure 3:
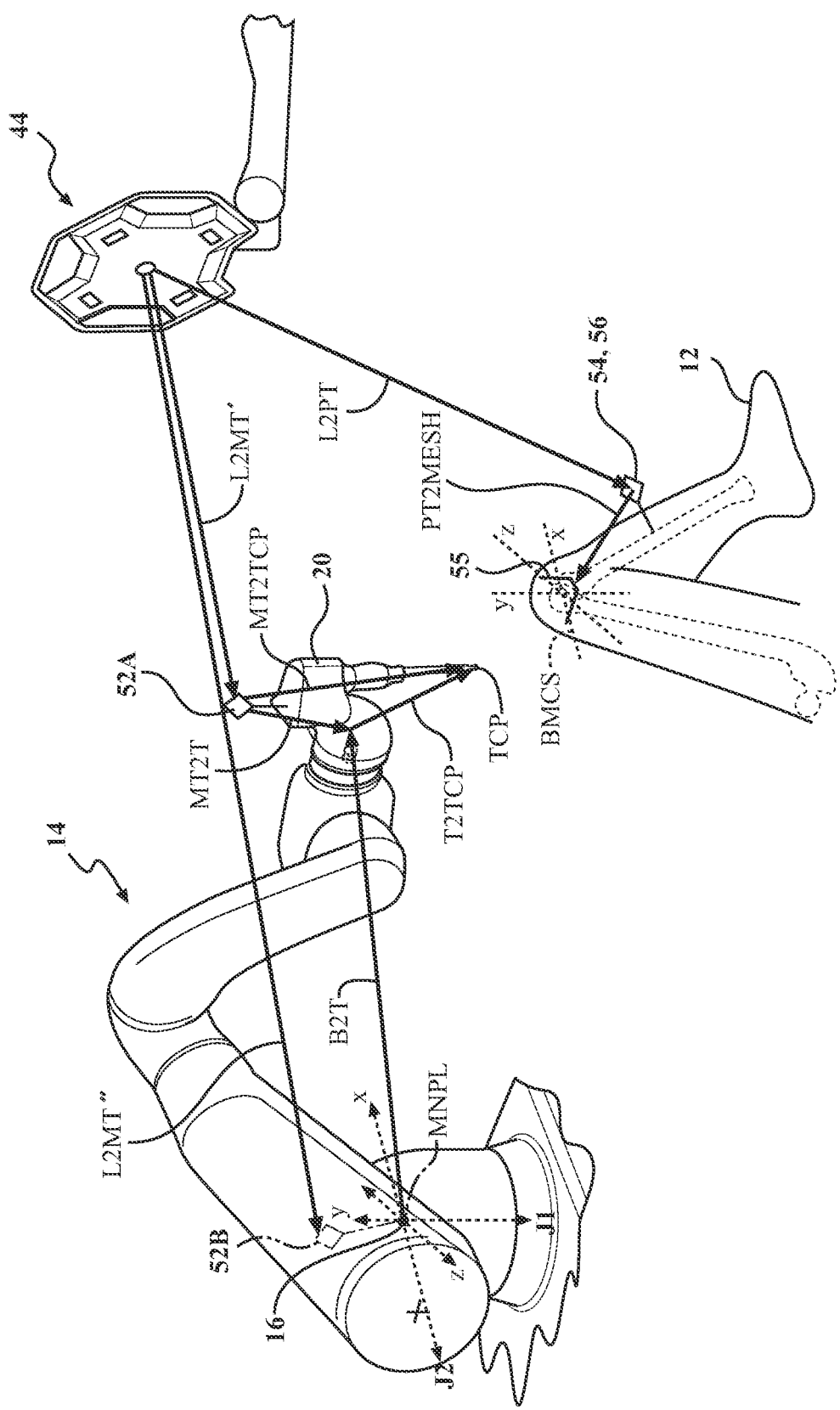
FIG. 3 is a perspective view illustrating transforms between components of a manipulator and components of a navigation system of the robotic surgical system, according to one embodiment.

As shown in FIG. 2, the controller 30 includes a boundary generator 66. The boundary generator 66 is a software module that may be implemented on the manipulator controller 60. Alternatively, the boundary generator 66 may be implemented on other components, such as the navigation controller 62. The boundary generator 66 generates virtual boundaries 55 for constraining the tool 20, as shown in FIG. 3. Such virtual boundaries 55 may also be referred to as virtual meshes, virtual constraints, or the like. The virtual boundaries 55 may be defined with respect to a 3-D bone model registered to the one or more patient trackers 54, 56 such that the virtual boundaries 55 are fixed relative to the bone model. The state of the tool 20 is tracked relative to the virtual boundaries 55. In one embodiment, the state of the TCP is measured relative to the virtual boundaries 55 for purposes of determining when and where haptic feedback force is applied to the manipulator 14, or more specifically, the tool 20.

A tool path generator 68 is another software module run by the controller 30, and more specifically, the manipulator controller 60. The tool path generator 68 generates a path 100 for the tool 20 to traverse, such as for removing sections of the anatomy to receive an implant. One exemplary system and method for generating the tool path 100 is explained in U.S. Pat. No. 9,119,655, entitled, "Surgical Manipulator Capable of Controlling a Surgical Instrument in Multiple Modes," the disclosure of which is hereby incorporated by reference. In some embodiments, the virtual boundaries 55 and/or tool paths 100 may be generated offline rather than on the manipulator computer 26 or navigation computer 36. Thereafter, the virtual boundaries 55 and/or tool paths 100 may be utilized at runtime by the manipulator controller 60. Yet another software module in FIG. 2 is a state comparison module 96, the details of which are described below.

II. Data Fusion and Filtering for Determining Commanded States of the Tool Relative to the Surgical Site As described above, the manipulator 14 and the navigation system 32 operate with respect to different coordinate systems, i.e., the manipulator coordinate system MNPL and the localizer coordinate system LCLZ, respectively. As such, in some embodiments, the controller 30 fuses data from the manipulator 14 and the navigation system 32 for controlling the manipulator 14 using the navigation system 32. To do so, the controller 30 utilizes data fusion techniques as described herein.

In general, the controller 30 acquires raw data of various transforms between components of the system 10. As used herein, the term "raw" is used to describe data representing an actual or true state of one or more components of the system 10 (e.g., base 16, tool 20, localizer 44, trackers 52, 54, 56) relative to at least another component(s) of the system 10, whereby the raw data is obtained near instantaneously (in near real time) from its respective source such that the raw data is unfiltered. The raw data is an unaltered or minimally processed measurement.

As used herein, the term "filtered" is used to describe raw data that is filtered according to a filter length and that represents a filtered state of one or more components of the system 10 relative to at least another component(s) of the system 10. The filtered data is delayed with respect to the near instantaneously obtained raw data due to application of the filter length in the filter. As will be described below, the raw data is ultimately filtered to control the manipulator 14. Additional details related to filtering are described below.

Each tracked component has its own coordinate system separate from the manipulator coordinate system MNPL and localizer coordinate system LCLZ. The state of each component is defined by its own coordinate system with respect to MNPL and/or LCLZ. Each of these coordinate systems has an origin that may be identified as a point relative to the origin of the manipulator coordinate system MNPL and/or the localizer coordinate system LCLZ. A vector defines the position of the origin of each of these coordinate systems relative to another one of the other coordinate systems. The location of a coordinate system is thus understood to be the location of the origin of the coordinate system. Each of these coordinate systems also has an orientation that, more often than not, is different from the coordinate systems of the other components. The orientation of a coordinate system may be considered as the relationship of the X, Y and Z-axes of the coordinate system relative to the corresponding axes of another coordinate system, such as MNPL and/or LCLZ.

Figure 6:
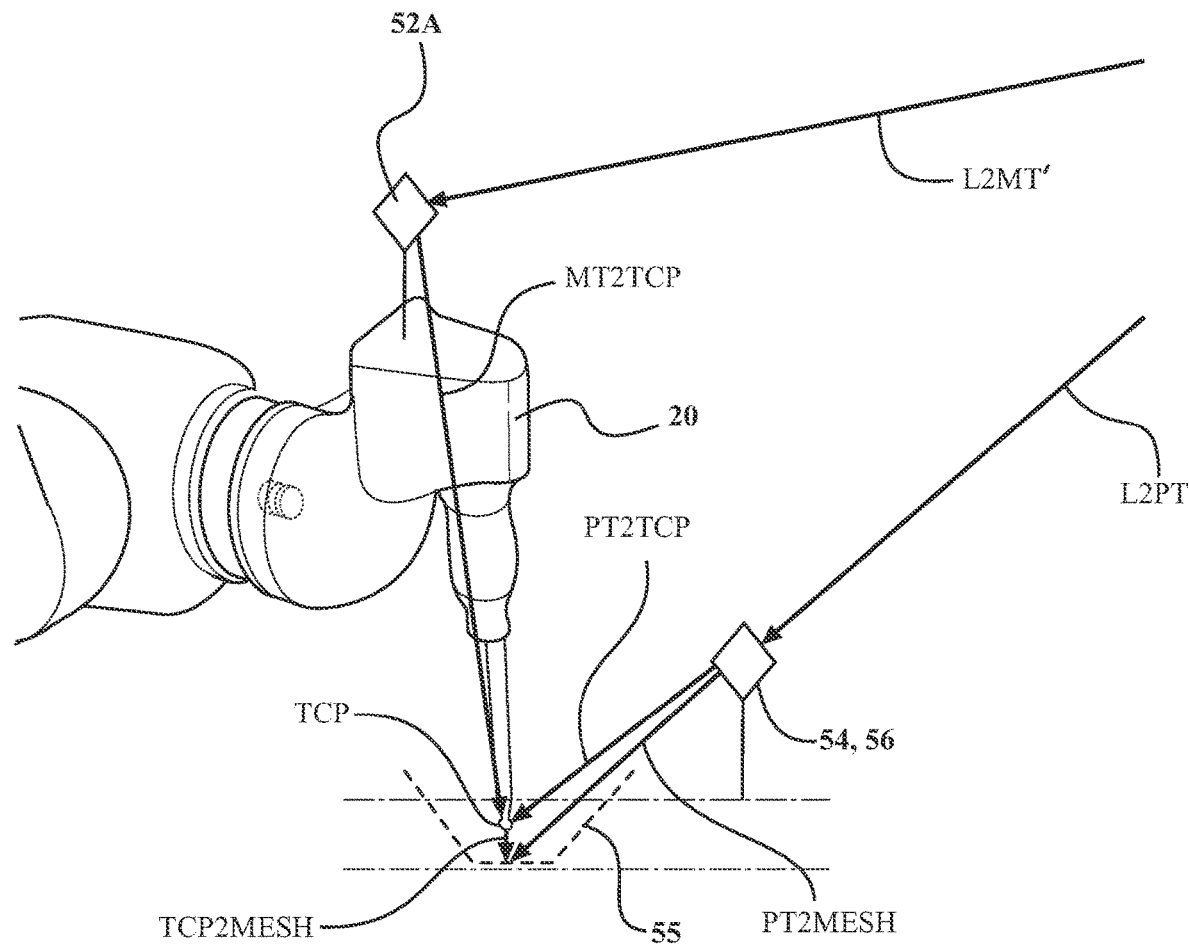
FIG. 6 is a perspective view illustrating transforms between a localizer, patient tracker, and manipulator tracker of the navigation system, a tool center point of the tool, and a virtual mesh associated with the target tissue, according to one embodiment.

Referring to FIGS. 3 and 6, the state of one component of the system 10 relative to the state of another component is represented as a transform (shown in the figures using arrows). In one embodiment, each transform is specified as a transformation matrix, such as a 4×4 homogenous transformation matrix. The transformation matrix, for example, includes three unit vectors representing orientation, specifying the axes (X, Y, Z) from the first coordinate system expressed in coordinates of the second coordinate system (forming a rotation matrix), and one vector (position vector) representing position using the origin from the first coordinate system expressed in coordinates of the second coordinate system.

The transform, when calculated, gives the state (position and/or orientation) of the component from the first coordinate system given with respect to a second coordinate system. The controller 30 calculates/obtains and combines a plurality of transforms e.g., from the various components of the system 10 to control the manipulator 14, as described below.

As shown in FIG. 3, the transforms include the following: transform (B2T) between the base 16 and the tool 20, transform (MT2T) between the manipulator tracker 52 and the tool 20, transform (L2MT') between the localizer 44 and the manipulator tracker 52 on the tool 20, transform (L2MT") between the localizer 44 and the manipulator tracker 52 at the base 16, transform (L2PT) between the localizer 44 and one or more of the patient trackers 54, 56, transform (MT2TCP) between the manipulator tracker 52 and the TCP, and transform (T2TCP) between the tool 20 and the TCP.

Referring to FIG. 6, additional transforms include transform (PT2TCP) between the one or more patient trackers 54, 56 and the TCP, transform (TCP2MESH) between the TCP and the virtual boundary 55, and transform (PT2MESH) between the one or more patient trackers 54, 56 and the virtual boundary 55.

One exemplary system and method for obtaining the transforms of the various components of the system is explained in U.S. Pat. No. 9,119,655, entitled, "Surgical Manipulator Capable of Controlling a Surgical Instrument in Multiple Modes," the disclosure of which is hereby incorporated by reference.

The output (e.g., values) of the transforms are regarded as raw data when obtained instantaneously (in near real time) and when unfiltered. Such raw data may be understood as being derived from a near transform, i.e., a near instantaneous determination of the state of one component of the system 10 relative to the state of another component. On the other hand, the output values of such transforms are regarded as filtered data when the values are filtered, such as for reasons described below.

The transforms are now described in detail. The controller 30 acquires raw kinematic measurement data relating to a state of the tool 20. The state of the tool 20 may be determined relative to the manipulator coordinate system MNPL. In some instances, the raw kinematic measurement data may relate to the state of the tool 20 relative to the base 16. The raw kinematic measurement data may be obtained from the manipulator controller 60. Specifically, as shown in FIG. 3, the controller 30 is configured to acquire the raw kinematic measurement data by acquiring one or more values of transform (B2T) between a state of the base 16 and the state of the tool 20. Here, the raw kinematic measurement data may be obtained from kinematic data of the manipulator 14. In particular, the controller 30 may acquire one or more values of the first transform (B2T) by applying a forward kinematic calculation to values acquired from the joint encoders 19. Thus, the state of the tool 20 can be determined relative to the manipulator coordinate system MNPL without intervention from the navigation system 32. In other words, the first transform (B2T) may be obtained irrespective of any measurements from the navigation system 32.

In FIG. 3, transform (B2T) is indicated by an arrow having an origin at the base 16 and extending to and having an arrowhead pointing to the tool 20. In one exemplary convention used throughout FIG. 3, the arrowhead points to the component having its state derived or specified relative to the component at the origin. Transform (B2T) may be determined using any suitable reference frames (coordinate systems) on the base 16 and the tool 20.

The controller 30 may further acquire known relationship data relating to the state of the manipulator tracker 52 relative to the tool 20. In general, the known relationship data may be derived from any known relationship between the manipulator tracker 52 and the tool 20. In other words, the manipulator tracker 52 and the tool 20 have a relationship that is known or calculatable using any suitable method. The manipulator tracker 52 and the tool 20 may be fixed or moving relative to each other. For example, the manipulator tracker 52 may be attached directly to the tool 20, as shown in FIG. 3. Alternatively, the manipulator tracker 52 may be attached to one of the links 18, which move relative to the tool 20. In general, the manipulator tracker 52 and the tool 20 are tracked by different techniques, i.e., by navigation data and kinematic measurement data, respectively. The known relationship data assists to bridge the kinematic measurement data and the navigation data by aligning the manipulator tracker 52 and the tool 20 to a common coordinate system.

The known relationship data may be fixed (constant or static) or variable. In embodiments where the known relationship data is fixed, the known relationship data may be derived from calibration information relating to the manipulator tracker 52 and/or the tool 20. For example, the calibration information may be obtained at a manufacturing/assembly stage, e.g., using coordinate measuring machine (CMM) measurements, etc. The known relationship data may be obtained using any suitable method, such as reading the known relationship data from a computer-readable medium, an RFID tag, a barcode scanner, or the like. The known relationship data may be imported into system 10 at any suitable moment such that the known relationship data is readily accessible by the controller 30. In embodiments where the known relationship data is variable, the known relationship data may be measured or computed using any ancillary measurement system or components, such as additional sensors, trackers, encoders, or the like. The known relationship data may also be acquired after mounting the manipulator tracker 52 to the tool 20 in preparation for a procedure by using any suitable technique or calibration method.

Whether static or variable, the known relationship data may or may not be regarded as raw data, as described herein, depending on the desired technique for obtaining the same. In one embodiment, the controller 30 may acquire the known relationship data by acquiring one or more values of transform (MT2T) between the state of the manipulator tracker 52A and the state of the tool 20. Transform (MT2T) may be determined with respect to any suitable coordinate system or frame on the manipulator tracker 52 and the tool 20.

In other embodiments, the controller 30 may determine transform (MT2T) using any one or more of kinematic measurement data from the manipulator 14 and navigation data from the navigation system 32 such that known relationship data is not utilized. For example, transform (MT2T) may be calculated using one or more of raw kinematic measurement data relating to the state of the tool 20 relative to the manipulator coordinate system MNPL from the manipulator 14 and raw navigation data relating to the state of the tracker 52 relative to the localizer 44 from the navigation system 32. For example, the tool 20 may be rotated about its wrist to create a circular or spherical fit of the tool 20 relative to the manipulator tracker 52.

In some embodiments, it may be desirable to determine the state of the TCP relative to the manipulator coordinate system MNPL and/or localizer coordinate system LCLZ. For example, the controller 30 may further acquire known relationship data relating to the state of the tool 20 relative to the TCP by acquiring one or more values of transform (T2TCP), as shown in FIG. 3. Additionally, or alternatively, the controller 30 may acquire known relationship data relating to the state of the manipulator tracker 52A relative to the TCP by acquiring one or more values of transform (MT2TCP), as shown in FIG. 3. Transforms (T2TCP) and (MT2TCP) may be acquired using any of the aforementioned techniques described with respect to transform (MT2T). Transforms (T2TCP) and (MT2TCP) may be utilized to determine commanded states 98 of the TCP relative to the surgical site, as well as actual states 108 of the same, as described in the subsequent section.

The controller 30 is further configured to acquire, from the navigation system 32, raw navigation data relating to the state of the manipulator tracker 52 relative to the localizer 44. The controller 30 may do so by acquiring one or more values of transform (L2MT') between the manipulator tracker 52A on the tool 20 and the localizer 44 and/or transform (L2MT") between the manipulator tracker 52B at the base 16 and the localizer 44. Transforms (L2MT' or L2MT") can be calculated using navigation data alone, irrespective of kinematic measurement data from the manipulator 14.

The transform (L2PT) between the localizer 44 and one or more of the patient trackers 54, 56 may be determined by the controller 30 by similar techniques and assumptions as described above with respect to transforms (L2MT' or L2MT"). Specifically, the localizer 44 is configured to monitor the state of one or more of the patient trackers 54, 56 and the controller 30 is configured to acquire, from the navigation system 32, raw navigation data relating to the state of the one or more of the patient trackers 54, 56 relative to the localizer 44.

Referring to FIG. 6, transform (PT2MESH) may be calculated between one or more of the patient trackers 54, 56 and the virtual boundary 55 associated with the anatomy of the patient 12 using registration techniques involving the navigation system 32 and the pointer (P). In one embodiment, the pointer (P) is tracked by the navigation system 32 via the pointer tracker (PT) and is touched to various points on a surface of the anatomy. The navigation system 32, knowing the state of the pointer (P), registers the state of the anatomy with respect to one or more of the patient trackers 54, 56. Alternatively, (PT2MESH) may be broken up into additional (intermediate) transforms that are combined to result in (PT2MESH). For example, transform (IMAGE2MESH) may correspond to implant placement (e.g., from surgical planning) relative to a pre-op image, acquired using techniques such as CT, MRI, etc., and transform (PT2IMAGE) may correspond to location of the one or more patient trackers 54, 56 relative to that same pre-op image (e.g., from registration). These intermediate transforms may be combined to obtain transform (PT2MESH). One exemplary system and method for registering the anatomy is explained in U.S. Pat. No. 9,119,655, entitled, "Surgical Manipulator Capable of Controlling a Surgical Instrument in Multiple Modes," the disclosure of which is hereby incorporated by reference.

In FIG. 6, two additional transforms are shown which relate to the TCP. Specifically, these transforms include transform (PT2TCP) between the one or more patient trackers 54, 56 and the TCP and transform (TCP2MESH) between the TCP and the virtual boundary 55. As will be described below, these transforms are utilized to determine actual and commanded states 98 of the tool 20 relative to the surgical site. Transforms (PT2TCP) and (TCP2MESH) may be determined using navigation data alone, or navigation data in combination with kinematic measurement data. Those skilled in the art appreciate that given the various components of the system 10, other transforms other than those described above may be utilized in the techniques described herein.

Figure 4:
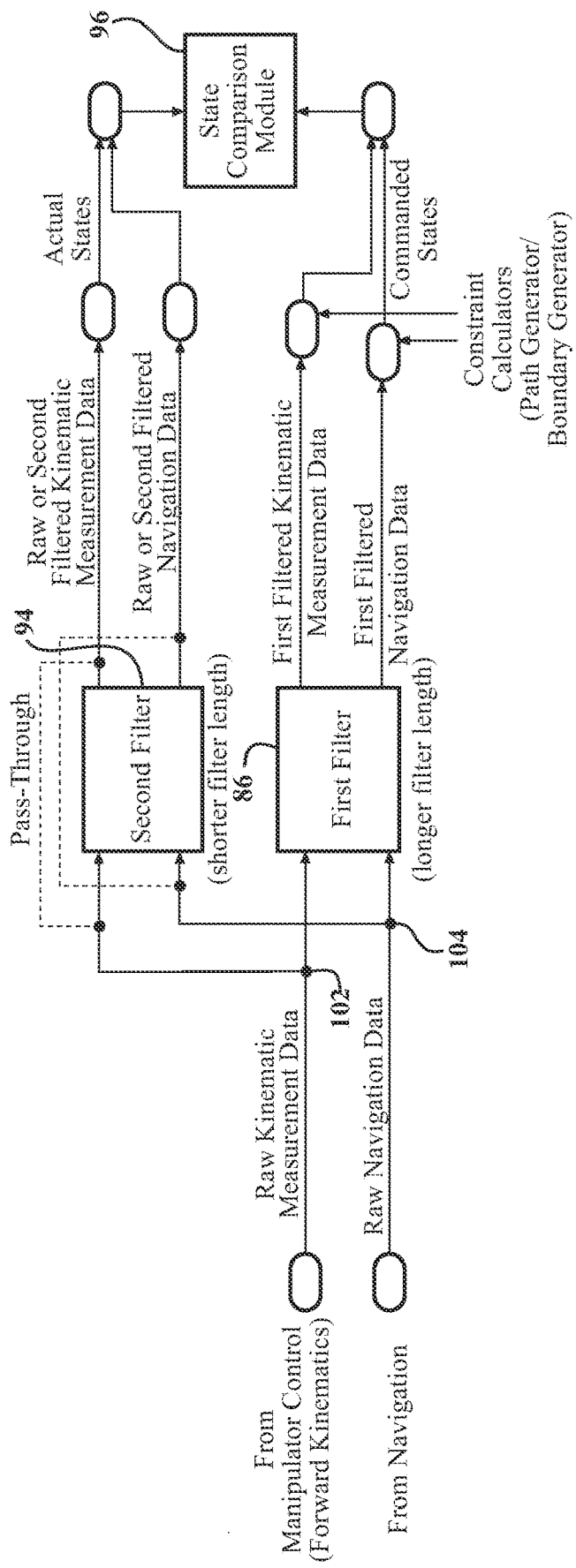
FIG. 4 is a simplified block diagram of techniques, implemented by the controller, for filtering and fusing data from the manipulator and the navigation system, according to one embodiment.

With the transforms identified, one simplified embodiment of the data fusion and filtering techniques is illustrated in FIG. 4. As shown, the controller 30 acquires the raw kinematic measurement data, which in this embodiment, relates to kinematically derived states of the manipulator 14. In one example, the raw kinematic measurement data may relate to the state of the tool 20 relative to the base 16 or manipulator coordinate system MNPL, i.e., (B2T)) Additionally or alternatively, the raw kinematic measurement data may relate to a state of one or more of the links 18 relative to the base 16, a state of the tool 20 relative to one or more of the links 18, a state of one or more of the joints (J1-J6) relative to the base 16, a state of the tool 20 relative to one or more of the joints (J1-J6), a state of the TCP relative to any of the aforementioned components, or the like. The controller 30 may acquire this raw kinematic measurement data using forward kinematic calculations, and by using any suitable transform depending on which components of the manipulator 14 have states that are being tracked.

The controller 30 is also configured to acquire, from the navigation system 32, raw navigation data. The raw navigation data may relate to the state of the manipulator tracker 52 relative to the localizer 44 (L2MT', L2MT") and/or data relating to the state of the one or more patient trackers 54, 56 relative to the localizer 44 (L2PT).

In FIG. 4, the raw kinematic measurement data and raw navigation data (i.e., raw data) is passed to a first filter 86. The first filter 86 applies a first filter length, to produce first filtered kinematic measurement data and first filtered navigation data, respectively. The first filtered measurement and navigation data are utilized to determine commanded states 98 of the tool 20 while commanding the tool 20 to move relative to the surgical site, e.g., along a tool path 100.

The first filter 86 is a digital temporal filter that filters the raw data. This filtering may occur in the time-domain. Filtering may be understood as performing a type of averaging over a time history of data. Filtering does not affect the update or measurement rate but rather the frequency of content of the output signal (e.g., how quickly or smoothly the output changes), yet still providing a new output for each sample. In general, the greater the filter length for the filter, the greater the filter latency (delay) and averaging. In other words, a greater filter length provides more time to take into account (or average) determinations of the raw data over time. Thus, the greater the filter length, the smoother the raw data is over time. As will be described below, this first filtered data is involved in the calculation of constraints and downstream control commands, ultimately used to control the manipulator 14. The first filter 86 may consequently result in spatial filtering by ultimately causing the manipulator 14 to lag (as compared with the second filtered data, described below) in the spatial domain.

The first filter 86 may be one or more of various types of filters. In one embodiment, the first filter 86 may be understood as averaging inputted data, or averaging a time history of data. For example, the first filter 86 may be an infinite impulse response (IIR) filter, a finite impulse response filter (FIR), a "boxcar" filter, or the like. In addition, the filter order and length or filter length maybe chosen to meet requirements of the application. Generally, the filtering described herein applies to low pass-type filtering, however, other filter-types, such as band pass, high pass, or notch filtering may be utilized. The filter length takes into account the time history of the filter. Examples of a filter length include a "time constant" for IIR filters, number of taps or coefficients (i.e., memory depth) for a FIR (finite impulse response) filter, or any parameter of a filter relating to the amount of depth of data that is processed or averaged. In addition, the filter order and length maybe chosen to meet requirements of the application. Generally, the filtering described herein applies to low pass-type filtering, however, other filter-types, such as band pass, high pass, or notch filtering may be utilized.

The filter length of the first filter 86 may be expressed as a unit of time. For example, the filter length may be represented in milliseconds (ms) or seconds (s). In one embodiment, the first filter length is greater than or equal to 100 ms and less than or equal to 1000 ms. For example, the first filter length may be 1000 ms. In this example, for any given time step, the filtered relationship is based on the raw relationship determinations averaged over the previous 1000 ms relative to the given time step.

Filtering by the first filter 86 is performed on the raw data for two primary purposes, i.e., reducing noise and increasing system stability. If it were possible, using the raw data alone to control the system 10 is would be preferred since doing so would give the fastest and most accurate response. However, filtering is needed because of practical limitations on the system 10. Such practical limitations include noise reduction and stability improvements by removal of positive feedback. The localizer 44 is capable of operating at a much higher bandwidth as compared to the manipulator 14. That is, the localizer 44 tracks poses of the trackers 52, 54, 56 faster than the manipulator 14 can respond. Controlling off the raw data alone causes instability of system 10 because the manipulator 14 must react to commanded movements including those arising from random signal variation (i.e., noise), which are provided at the rate of the localizer 44. For example, the manipulator 14 would have to respond to every variation in the raw data. Commanded movement occurring at a rate higher than the manipulator 14 can respond results in heat, audible noise, mechanical wear, and potentially resonance, which can cause system instability. Because the localization data feedback represents an outer positioning loop, it is important not to close this outer loop at a higher bandwidth than the manipulator 14 can respond, to avoid instability.

Filtering with the first filter 86 reduces the bandwidth of the outer positioning loop thereby accommodating the bandwidth limitations of the inner positioning loop of the manipulator 14. Through such filtering, noise is reduced and stability is improved by removal or reduction in positive feedback. The manipulator 14 is prevented from reacting to every minor change in the raw data. Otherwise, if the manipulator 14 had react to noisy data, the manipulator 14 may be susceptible to spatial overshoot of tool 20 along the tool path 100 (such as when turning corners). Such spatial overshoot may cause the tool 20 to overcut the anatomy contrary to best design practices of favoring undercutting rather than overcutting. Instead, filtering of the raw data causes the manipulator 14 to behave more smoothly and run more efficiently. Further, noise may be introduced into the system 10 through measurement error in the sensors (e.g., encoders, localization feedback data, etc.). Filtering limits overall noise to a threshold tolerable by the system 10.

Figure 5:
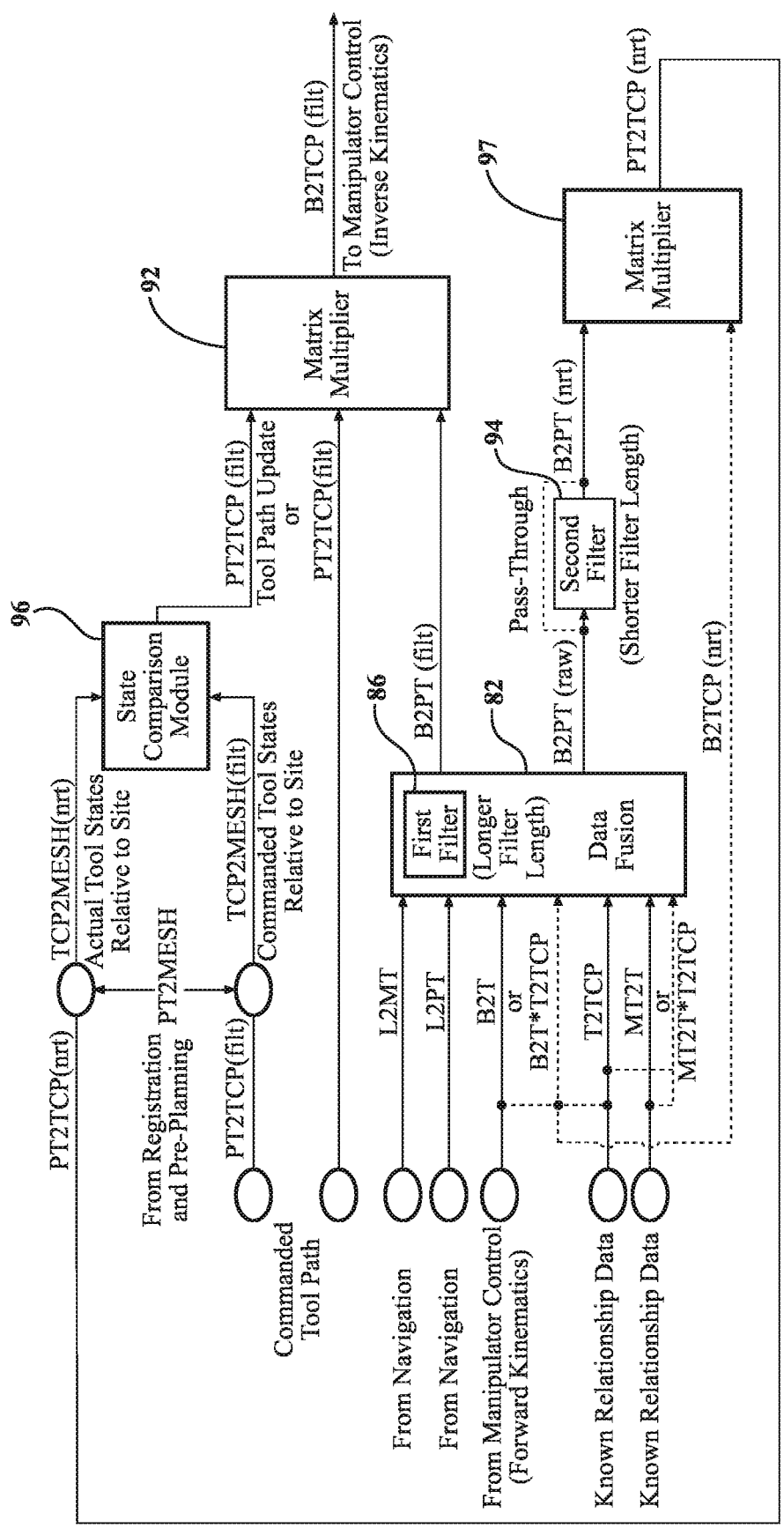
FIG. 5 is a detailed block diagram of techniques, implemented by the controller, for filtering and fusing data from the manipulator and the navigation system, according to one embodiment.

FIG. 5 is a block diagram illustrating, in part, aspects of the data fusion techniques implemented by the controller 30 and as described herein. In this section, only those portions of FIG. 5 relating to generating commanded states 98 of the tool 20 relative to the surgical site are described. As shown, the transforms (L2MT, L2PT) are provided from navigation data, transform (B2T) is provided from kinematic measurement data, and transforms (T2TCP, MT2T) are provided from known relationship data, as described above. As shown, transforms (B2T) and (T2TCP) may be combined from kinematic measurement data and known relationship data to form transform (BT2TCP) between the base 16 and the TCP. Similarly, transforms (MT2T) and (T2TCP) may be combined from known relationship data to form transform (MT2TCP) between the manipulator tracker 52 and the TCP.

The controller 30 combines any combination of these transforms from different sources at data fusion block 82. The controller 30 may apply any suitable matrix multiplier at data fusion block 82. The output of the data fusion block 82 is transform (B2PT) between the base 16 and one or more of the patient trackers 54, 56. However, transform (B2PT) is filtered by the first filter 86, and hence is identified in FIG. 5 using the abbreviation "filt" representing a filtered version of this transform. Filtered transform (B2PT) may be understood as representing first filtered states of the one or more patient trackers 54, 56 relative to the base 16. The first filter 86 is shown within the data fusion block 82 in FIG. 5. However, the first filter 86 may be applied at the output of the data fusion block 82 instead. Filtered transform (B2PT), which is based on pose data, is primarily or entirely a spatial relationship. However, the sequences of such pose data may also signify one or more relationships that are derived from spatial parameters, such as relationships with respect to velocity and/or acceleration of the respective components of the transform.

In one embodiment, transform (B2PT) is formed by combining transforms (B2T), (MT2T), (L2MT'; localizer 44 to tool tracker 52A) and (L2PT). Transforms (MT2T) and (L2MT') may be inverted to enable proper combination these transforms. In another embodiment, transform (B2PT) is formed by combining transforms (L2MT"; localizer 44 to base tracker 52B) and (L2PT). Those skilled in the art appreciate that transform (B2PT) may be formed using any other suitable combination of transforms from kinematic measurement, navigation, and/or known relationship data.

The one or more patient trackers 54, 56 are assumed to move during operation of the system 10. Movement of the patient trackers 54, 56 may result from movement of a table on which the patient 12 rests, movement of the patient 12 generally, and/or local movement of the anatomy subject to the procedure. Movement may also occur from anatomy holder dynamics, cut forces affecting movement of the anatomy, and/or physical force applied to the anatomy by an external source, i.e., another person, or a collision with an object. As such, it is desirable to provide the first filter 86 or a different filter to transform (L2PT) to enable the manipulator 14 to track/respond to motion within practical limits needed for stability. Such filtering is utilized for many of the same reasons described above with respect to the first filter 86, i.e., signal noise reduction and increasing system stability.

As shown in FIG. 5, the controller 30 combines filtered transform (B2PT) and the filtered version of transform (PT2TCP) to produce filtered transform (B2TCP) between the base 16 and the TCP. The controller 30 produces this transform by utilizing matrix multiplier at block 92. The controller 30 utilizes filtered transform (B2TCP) for controlling the manipulator 14 using inverse kinematic calculations wherein the path generator 69 generates the tool path 100 based on the filtered transform (B2TCP) and such that the boundary generator 66 assesses the filtered transform (B2TCP) with respect to the virtual boundaries 55. Mainly, filtered transform (B2PT) may be combined with filtered transform (B2TCP) to produce filtered transform (PT2TCP) between the one or more patient trackers 54, 56 and the TCP. As shown in FIG. 5, filtered transform (PT2TCP) may be combined with transform (PT2MESH) from registration and pre-planning to produce filtered transform (TCP2MESH). Ultimately, filtered transform (TCP2MESH) represents command states of the tool 20, and more specifically the TCP, relative to the surgical site.

III. Techniques for Determining Actual States of the Tool Relative to the Surgical Site and Comparing Actual States to Commanded States In the embodiments of the techniques described above, the raw kinematic measurement and/or raw navigation data are filtered individually, or in combination, for determining commanded states 98 of the tool 20. Notably, the raw kinematic measurement and raw navigation data remain available prior to being filtered in FIG. 4. This raw data is exploited for techniques for modifying operation of the tool 20, as described in detail below.

In FIG. 4, the raw data remain available and are duplicated or accessed and passed to the branch including the second filter 94, leaving the first filtered measurement and/or navigation data in tact for control purposes downstream. The second filter 94 applies a second filter length that is shorter than the first filter length, to produce raw or second filtered kinematic measurement data and raw or second filtered navigation data, respectively. The raw or second filtered measurement and navigation data are utilized to determine actual states 108 of the tool 20 relative to the surgical site. The state comparison module 96 compares the actual states 108 and commanded states 98. The second filtered data is produced specifically for comparison to the first filtered data to determine how to modify operation of the tool 20 based on the outcome of the comparison.

Utilizing the raw kinematic measurement and navigation data before filtering by the first filter 86 enables the controller 30 to record to memory a log of actual states 108 of the tool 20. The controller 30 is configured to determine actual states 108 of the tool 20 while commanding the tool 20 to move relative to the surgical site, e.g., along the tool path 100. As will be described below, the actual states 108 are determined using one or more of second filtered (or unfiltered) kinematic measurement data and second filtered (or unfiltered) navigation data. For any given time step during movement of the tool 20, each commanded state 98 has a corresponding actual state 108. As described above, the first filter 86 generally has a longer filter length to accommodate stability requirements of the outer position loop. Thus, these actual states 108 are in contrast to the commanded states 98, which are otherwise delayed by filtering by the longer filter length of the first filter 84. Accordingly, the term 'actual' as used herein is not intended to be limited solely to instantaneous states of the tool 108. Said differently, the raw kinematic measurement data and/or raw navigation data is lightly filtered relative to the filtering of the first filtered measurement and/or navigation data. The actual states 108 may be purely instantaneous (unfiltered) or more instantaneous (less filtered) than the commanded states 98.

In one embodiment, the controller 30 is configured to utilize the raw kinematic measurement and/or navigation data (instead of the second filtered measurement and/or navigation data), e.g., from any one or more of the transforms, to determine the actual states 108. The raw kinematic measurement and/or navigation data, in this embodiment, are filtered by the second filter 94 having a filter length of zero. If filtered by the filter length of zero, the raw kinematic measurement and/or navigation data "passes through" the second filter 94, as shown in FIGS. 4 and 5.

The raw data are filtered by the second filter 94 to remove high frequency noise or high frequency jitter from the raw signal. The amount of filtering (filter length) applied by the second filter 94 may be chosen such that it is long enough to remove the aforementioned high frequency noise/jitter in the raw signal, but short enough to represent the near real time states of the tool 20 to the extent practical. When filtered, it is generally understood that the filter length is greater than zero. In one example, the filter length of the second filter 94 is greater than 0 ms and less than or equal to 50 ms, as compared to, for example, the filter length of 1000 ms for the first filter 86. The second filter 94 may have any configuration and may be any type of filter as those described above with respect to the first filter 86.

The controller 30 is configured to filter any of the raw data with the second filter 94 (e.g., from any one or more of the transforms of FIGS. 3 and 6) to arrive at the actual states 108. However, in one specific embodiment, as shown in FIG. 5, the actual states 108 are derived using the following technique. Any suitable combination of the transforms of FIG. 5 are combined in the data fusion block 82. Another output of the data fusion block 82 is transform (B2PT) between the base 16 and one or more of the patient trackers 54, 56. However, transform (B2PT) is raw, and hence is identified in FIG. 5 using "raw" representing a raw version of this transform. Raw transform (B2PT) may be understood as representing raw states of the one or more patient trackers 54, 56 relative to the base 16. The raw transform (B2PT) then passes to the second filter 94, which applies the shorter filter length of 0 (pass-through) or for example, between 0-50 ms (i.e., lightly filtered). Assuming the filter length is greater than 0, a near real time (i.e., "nrt") transform (B2PT) is produced.

As shown in FIG. 5, the controller 30 combines near real time transform (B2PT) and a near real time version of transform (BT2TCP), which is extracted from the transforms before input into the data fusion block 82. The combination of these transforms produces a near real time transform (PT2TCP) between the one or more patient trackers 54, 56 and the TCP. The controller 30 produces near real time transform (PT2TCP) by utilizing matrix multiplier at block 97. Near real time transform (PT2TCP) may be combined with transform (PT2MESH) from registration and pre-planning to produce near real time transform (TCP2MESH). Ultimately, near real time transform (TCP2MESH) represents actual states 108 of the tool 20, and more specifically the TCP, relative to the surgical site.

Those skilled in the art appreciate that various other combinations of transforms, other than those described herein may be utilized to determine actual states 108 of the tool 20, and/or TCP relative to the surgical site, and that such various combinations may depend on any factors, such as the location of the object being tracked, the desired coordinate system, or the like.

As described in the previous section, filtered transform (PT2TCP) is produced and represents commanded states 98 of the tool 20, and more specifically the TCP, relative to the surgical site. The values from the near real time and filtered transform (TCP2MESH) are inputted into the comparison module 96. The state comparison module 96 determines deviations 110 between the commanded states 98 and the actual states 108. Consequently, the commanded states 98 are compared to the actual states 108 to properly account for actual states that may be different than commanded states of the tool 20 or TCP. For example, as described in the next section, the controller 30 determines tool path 100 or feed rate updates/modifications for the tool 20 based on an outcome of this comparison.

The deviations 110 may be represented with respect to any components of the pose of the tool 20. In one sense, the deviations 110 may be understood by a difference (subtraction) between the commanded and actual states 98, 108. These deviations 110 can be identified by the state comparison module 96, which compares the underlying data respectively corresponding to the commanded and actual states 98, 108.

Deviations 110 between the commanded and actual states 98, 108 may not always occur. For example, there may be situations where the state of the tool 20 or TCP is constant, enabling temporary alignment between the commanded and actual states 98, 108. However, more likely than not, such deviations 110 occur because of sudden or abrupt changes in movement of the tool 20 or TCP. In general, the more abrupt the change in movement of the tool 20 or TCP for any given time step, the greater the deviation 110 will be between the commanded and actual states 98, 108. Of course, the commanded and actual states 98, 108 may have any relationship with respect to each other and may deviate according to any manner depending on factors such as the type of data being compared (e.g., measurement or navigation data) and the respective filter lengths of the first filter 86 and the second filter 94, and the like.

Comparison between the commanded and actual states 98, 108 over time may be executed according to various implementations. In one example, the deviations 110 are converted into respective positional and angular components. The state comparison module 96 may perform this conversion to analyze each of the components individually.

In some embodiments, the deviations 110, or components thereof, may be taken "as-is" such that the state comparison module 96 accounts for an entirety of such deviations 110. Alternatively, the controller 30 is configured to compare the deviations 110 to one or more predetermined thresholds. For example, the positional and angular components of the deviations 110 are compared to one or more thresholds. If the deviation 110 exceeds the threshold, the deviation 110 is accounted for by the controller 30 for purposes of modifying operation of the tool 20.

In some instances, it may be undesirable to account for an entirety of the deviation 110 for any one or more of the positional and angular components. For example, the sensitivity of the threshold should be set such that only noticeable and/or meaningful deviations 110 exceed the threshold. In one example, the threshold should be greater than zero such that minor or negligible deviations 110 are disregarded. The threshold for the positional and/or angular components may be chosen based on cutting guidelines for the system 10. For example, the threshold may be set according to a predetermined distance or range (e.g., 1 mm) such that there is some safety margin to prevent over cutting of the target tissue, but sensitive enough to detect meaningful deviations 110 between the commanded 98 and actual states 108. The threshold may be an upper threshold or a lower threshold and may have any suitable limit, minimum, maximum, range, standard deviation from profile, or other configuration.

The state comparison module 96 may be implemented by the manipulator controller 60, as shown in FIG. 2. The state comparison module 96 may comprise any suitable computer-executable instructions, algorithms, and/or logic for comparing the raw/second filtered data to the first filtered data.

IV. Techniques for Modifying Tool Operation Based on Comparing Actual and Commanded States of the Surgical Tool Relative to the Surgical Site Based on an outcome or result of comparing commanded and actual states 98, 108 relative to the surgical site, the controller 30 dynamically modifies operation of the tool 20 relative to the surgical site. Such modification of tool 20 operation may be performed according to various techniques, but generally are focused on modifying the path of movement and/or the feed rate of the tool 20.

Although the tool 20 is subject to many of the techniques described herein, and it should be understood that because the TCP derived from the tool 20, the TCP similarly may be subject of these techniques, even when not explicitly stated.

Generally, the commanded states 98 are utilized to move the tool 20 relative to the surgical site. As shown in FIGS. 7-10, for example, such movement of the tool 20 may be along a commanded first path 100C.

To implement such modification, in one embodiment, the controller 30 determines a subsequent (follow-up) path 100' for the tool 20 to account for the deviations 110 between the commanded and actual states 98, 108. That is, the controller 30 provides a subsequent correction of the first path 100.

Figure 7:
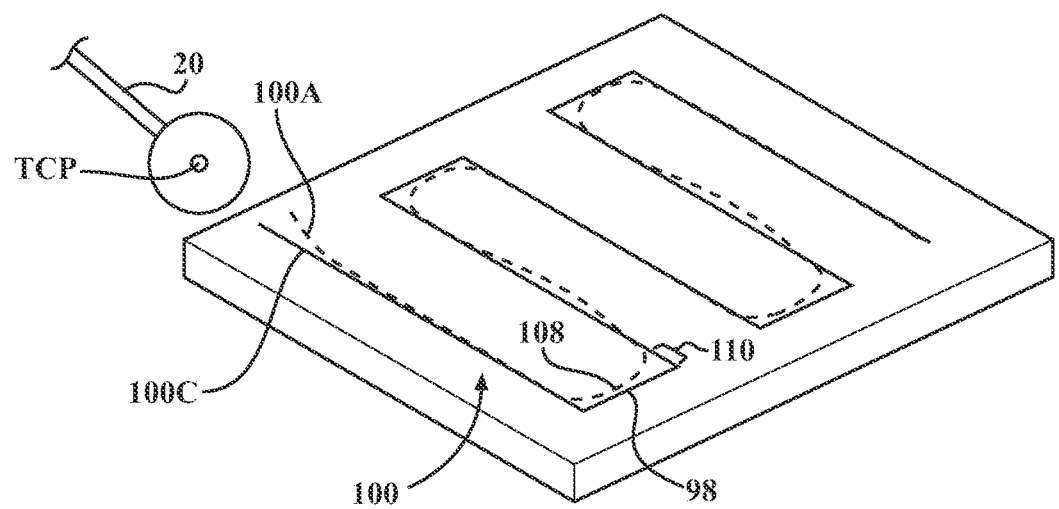
FIG. 7 is a diagram, according to one embodiment, illustrating sample movement of the tool along a first path for removing a portion target tissue wherein deviations between commanded and actual states of the tool are represented.

FIG. 7 is a diagram illustrating one example of the commanded and actual states 98, 108 of the tool 20 along the first path 100 with respect to time. In this example, the first path 100 is a cutting path for manipulating a target tissue at the surgical site. The tool 20 is commanded to move along the first path 100 for removing a first section of the target tissue. As shown, the tool 20 is commanded to move along the commanded first path 100C according to the commanded states 98. The commanded first path 100C is defined by a combination of all commanded states 98 with respect to time. However, because the commanded states 98 are derived from first filtered data, the tool 20 does not completely follow the commanded first path 100C. Instead, the tool 20 follows the actual states 108 as shown in FIG. 7, which are determined based on raw or second filtered data. In doing so, the tool 20 slightly deviates from the commanded first path 100C and follows an actual first path 100A, which is defined by a combination of all actual states 108 with respect to time. Here, the deviations 110 between the commanded and actual states 98, 108 over time are represented in FIG. 7 by a variable gap between the commanded and actual first paths 100C, 100A.

Figure 8:
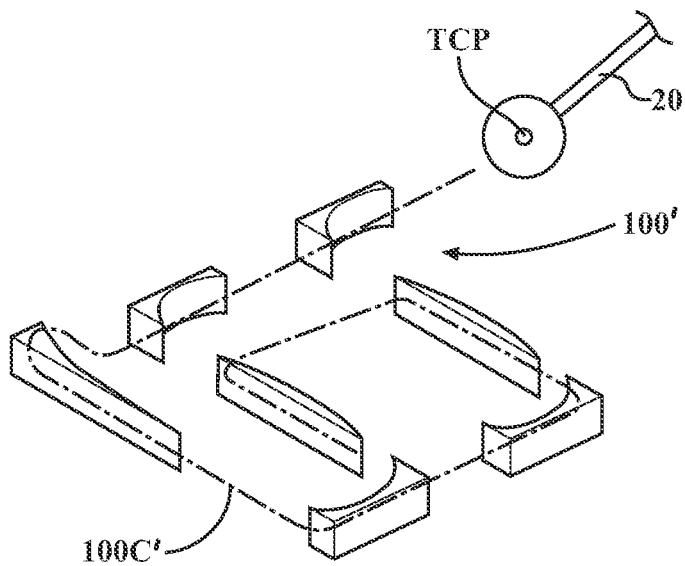
FIG. 8 is a diagram illustrating sample movement of the tool along a subsequent path for removing portions of the target tissue remaining from FIG. 7.

In FIG. 7, it has been demonstrated that the tool 20 follows the actual first path 100A instead of the commanded first path 100C. As a result, the tool 20 removes the first section of the target tissue as defined by the actual first path 100A rather than by the commanded first path 100C. If the system 10 proceeded on the basis that the tool 20 followed the commanded first path 100C alone, then the system 10 may falsely assume that the tool 20 removed the first section of tissue as commanded and as desired. However, FIG. 7 demonstrates that this is not the case. Specifically, certain peaks or uncut portions of the first section may remain because of the deviations 110. For simplicity, these peaks or uncut portions left over from the first section are referred to as the second section, which are illustrated in FIG. 8. In this specific example, the commanded first path 100C alone may be suitable for removing a "bulk" portion of the target tissue. However, in this example, the commanded first path 100C alone may be inadequate for "fine" removal of the residual target tissue.

As such, as shown in FIG. 8, the controller 30 generates the second path 100' as a follow-up path to account for the deviations 110 between the commanded and actual states 98, 108. In other words, the second path 100' is designed for more accurately or "finely" removing the target tissue, and more specifically, the second section left behind after commanding the tool 20 to move along the commanded first path 100C.

In one example, the second path 100' may be generated similarly to the first path 100 in that the controller 30 may determine (second) commanded states 98' for moving the tool 20 along a second commanded path 100C'. As such, any of the details described above with respect to generating of the first path 100 may apply to the second path 100'. However, even if commanded, the commanded second path 100C' is different than the commanded first path 100C in that the commanded second path 100C' accounts for the deviations 110 between the commanded and actual states 98, 108, whereas the commanded first path 100C does not. For this reason, the commanded second path 100C' in FIG. 8 follows a different route than the commanded first path 100C in FIG. 7.

The second path 100' may also be generated when the TCP is tracked to determine the deviations 110. In this example, a solid body model of the tissue, which is removed based on data from the actual states 108, may be utilized to determine what needs to be removed in second path 100'. The diameter of the TCP may be taken into account to determine what was actually removed from the surgical site. In one embodiment, if there are any deviations 110 between the commanded and actual states 98, 108 of the TCP, but the commanded and actual states 98, 108 overlap in a way that the TCP removes all the tissue from its actual states 108, such deviations 110 from the commanded states 98 may be disregarded to increase efficiency of the second path 100' and to avoid cutting when the tissue has already been removed.

The techniques described above for comparing the commanded and actual states 98, 108 from the first path 100 may be similarly applied to the commanded and actual states 98', 108' from the second path 100' to generate yet another path, e.g., a third path. Through this iterative process, any number of paths may be generated, thereby gradually removing the target tissue until a suitable state of the target tissue is achieved. In one example, this iterative process may be understood in that each currently generated path is designed to remove target tissue according to a level of accuracy that is greater than a preceding generated path. Said differently, the deviations 110 between commanded and actual states 98, 108 for any current path should have magnitudes being less than the deviations 110 between commanded and actual states 98, 108 for the preceding path.

Hence, in this "follow-up" or "clean-up" path embodiment, the error, i.e., the deviations between the commanded and actual bone surfaces (derived from transform between near real time capture of TCP path and commanded TCP path) are detected and under-cut errors (predominant) are corrected with the subsequent tool path 100' pass or passes until the residual error is within a pre-determined tolerance.

Although the technique of this embodiment has specific benefits, there may be drawbacks. For example, it will be apparent to the user that deviations 110 are occurring and corrections of such deviations 100 take time. Further, since most deviations 110 are likely to occur in corners or over disparate places on the cut surface, there is wasted time as the tool 20 "air cuts" from undercut area to undercut area. Additionally, if the second path 100' is not performed until the end of machining, early undercut errors may be amplified due to "regenerative cutting error" since undercut areas will impose greater tool forces than in non-undercut areas, thereby causing a greater undercut on the next pass, i.e., positive feedback. The next embodiment addresses some of these setbacks.

Figure 9:
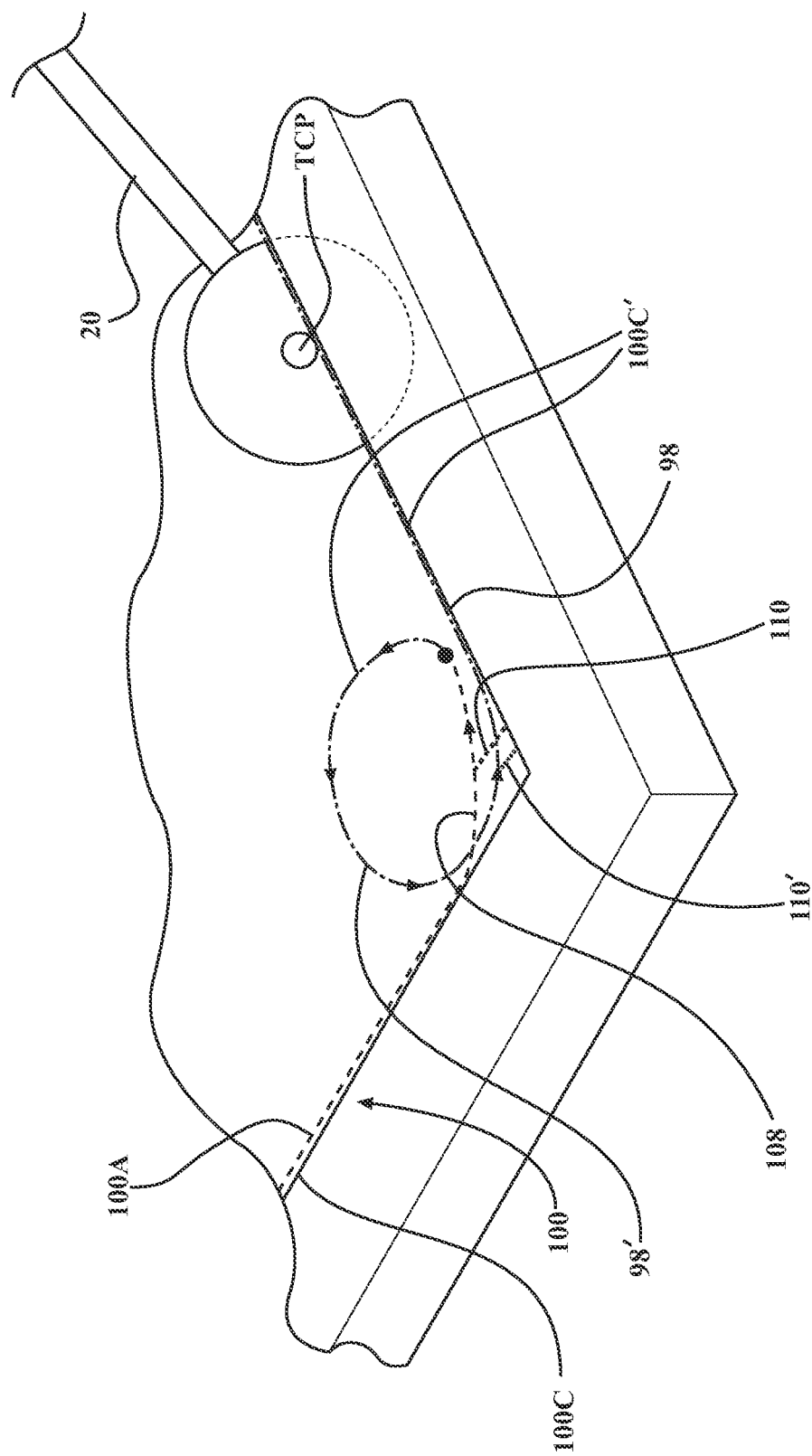
FIG. 9 is a diagram illustrating sample movement of the tool along a path of movement and immediate correction of the path based on recognition of present deviations between commanded and actual states.

In another embodiment as shown in FIG. 9, the controller 30, based on the outcome of comparing the commanded and actual states 98, 108, immediately modifies operation of the tool 20 along the path 100 to account for the deviations 110. This may be done, for example, by immediately altering the path 100. Alternatively, or additionally, the controller 30 may immediately alter a feed rate of the tool 20, as described below.

In the example of FIG. 9, a single tool path 100 is shown and as compared with FIG. 8, there is no subsequent tool path 100'. Here, the tool 20 follows the commanded path 100C, and actual states 108 of the tool 20 deviate from the commanded states 108 near a corner thereby causing deviations 110, which produce an undercut. Upon immediately recognizing these deviations 110, the controller 30 generates an updated commanded tool path 100C' with updated commanded states 98'. This immediate updating occurs at a point in time represented by a dot on the commanded tool path 100C. The updated commanded tool path 100C' loops back around with a localized clean up pass, thereby minimizing deviations 110'. In FIG. 9, the updated commanded tool path 100C' may continue along the originally commanded path 100C or any other suitable updated commanded tool path 100C'.

Using such "immediate" correction, the undercut is corrected before the remainder of the tool path 100 is executed. Due to the need for the first filter 86 to prevent positive feedback in the machining control loops, actions to address the undercut deviations 110 must occur, at a minimum, after the filter length of the first filter 86. One exception to this is to slow down the feed rate of the tool 20 along the tool path 100, which may be done in near real time (within the acceleration limits of the manipulator 14). As soon as the undercut deviation 110 is recognized, the commanded speed can be reduced. This action alone will often largely mitigate undercut deviation 110 because such errors are often caused by increases in machining force due to bone density increases or movement of the bone away from the tool 20. Any undercut occurring during the transient will be minimized When the deviation 110 falls below a tolerance threshold, the initial undercut error is then corrected with the localized cleanup pass, thereby removing the potential for regenerative cutting error development.

One method of addressing the initial undercut deviation 110 is to reverse the direction of feed and iteratively traverse a location of the undercut deviation 110 until the undercut is removed. This may be done with or without the aforementioned immediate feed rate slowdown, such as when the undercut deviation 110 is reduced below the tolerance threshold. That is, the undercut is sensed, but not acted upon until after the situation causing the undercut has ended. For example, large actuator accelerations commanded when turning a sharp corner at a high feed rate may not be achievable by the system 10, resulting in an undercut. Upon stabilizing on a subsequent low radius or straight area, the system 10 would sense that undercutting has stopped. The direction of feed would then reverse to go back along the tool path 100 to address the undercut, most likely at a lower feed rate. Feed rate may be ramped down and/or the re-transited path iterated until the undercut deviation 110 is reduced to the tolerance threshold.

In a situation where the tool path 100 is creating a pocket several times greater than the TCP diameter, a more sophisticated method of addressing the undercut deviation 110 would be to circle back to the undercut location using a circle having a radius, which the system 10 can follow with low error given its feed rate. In some instances, however, the circular/helical path milling may only be used to address undercut deviation 110, and then the original tool path 100 would be resumed until the next undercut deviation 110 is sensed.

Figure 10:
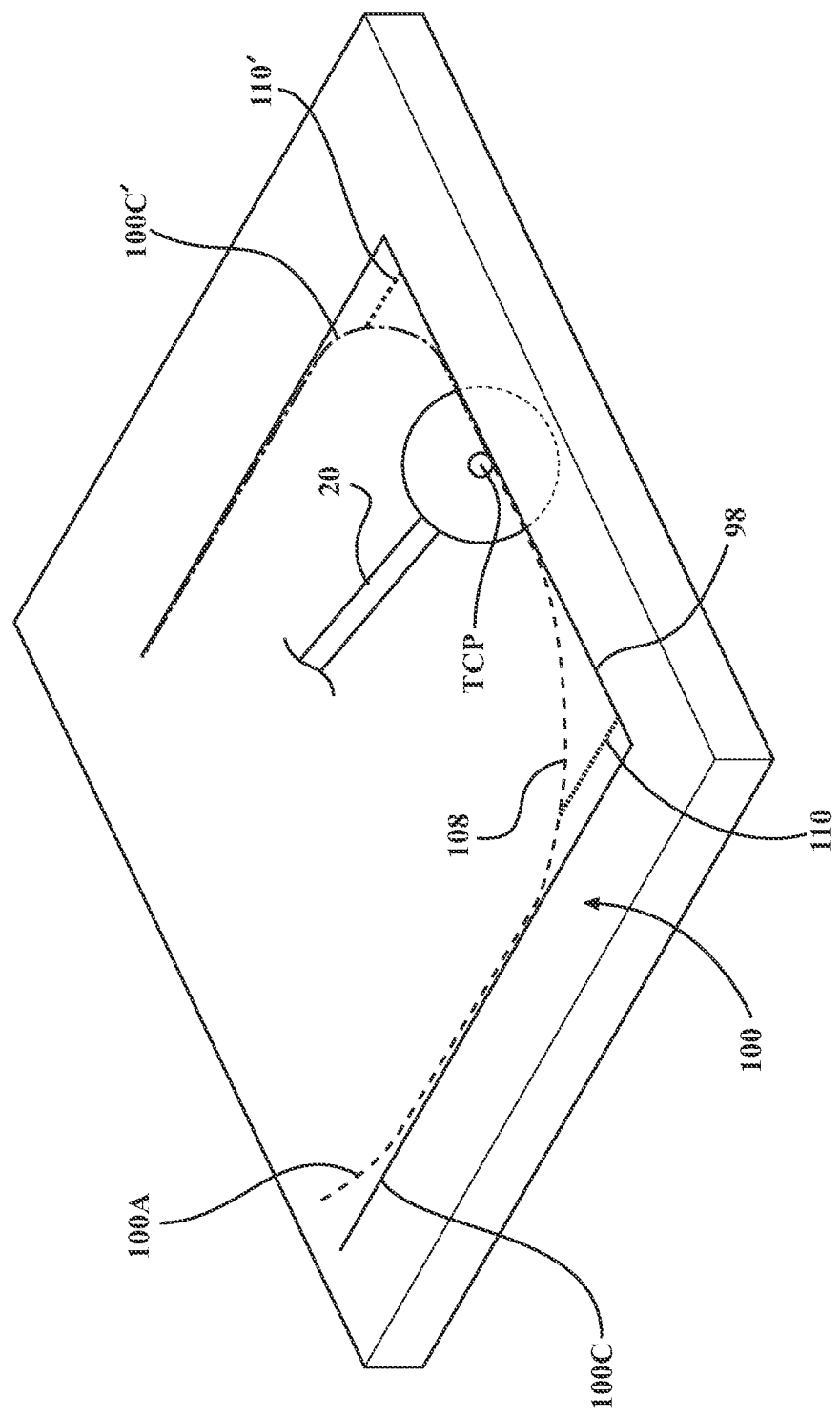
FIG. 10 is a diagram illustrating sample movement of the tool along a path of movement and proactively correction of the path based on recognition of past deviations between commanded and actual states.

In a third embodiment, as shown in FIG. 10, the controller 30, based on the outcome of comparing the commanded and actual states 98, 108, proactively modifies operation of the tool 20 along the path 100 to account for the deviations 110. This may be done, for example, by proactively altering the path 100. Alternatively, or additionally, the controller 30 may proactively alter the feed rate of the tool 20, as described below.

Once again, in the example of FIG. 10, a single tool path 100 is shown and as compared with FIG. 8, there is no subsequent tool path 100'. Here, the tool 20 follows the commanded path 100C, and actual states 108 of the tool 20 deviate from the commanded states 108 near a first corner thereby causing deviations 110, which produce the undercut. Upon immediately recognizing these deviations 110, the controller 30 proactively generates the commanded tool path 100C'. This proactive updating occurs at a point in time represented by the present location of the TCP in FIG. 10. The proactively generated and updated commanded tool path 100C' is configured to minimize deviations 110' at a second corner (as compared to the deviations 110 from the first corner). Thus, the controller 30, in a sense, predicts future undercuts and modifies operation of the tool 20 accordingly. In FIG. 10, the proactively updated commanded tool path 100C' may continue along the originally commanded path 100C or any other suitable updated commanded tool path 100C'.

In proactive correction, the system 10 learns from the prior undercut deviations 110 and adjusts the feed rate and/or tool path accordingly before similar deviations 110 can occur, thereby avoiding the need for subsequent correction. Due to the high variation in bone density, the preferred implementation of proactive correction is reduction in feed rate. Tool path corrections would need to be approached conservatively to avoid potential overcorrection or overcut "correction" error.

In this embodiment, the threshold value to proactively correct deviations 110 may be variable. For example, the threshold value may be dependent on whether the machining is a roughing pass or finishing pass. Alternatively, or additionally, the threshold value may be dependent on the function and criticality of the feature being machined. For example, lower undercut errors would likely be tolerable in the middle ⅔rds of a surface intended for a press fit interface. This is since undercuts in this region would result in rocking of the implant, which could lead to poor fixation and/or alignment. Larger undercuts would be allowable in the outer portion since bone is not strictly rigid and, within localized areas, highpoints can compress and adapt to the implant upon impaction.

The controller 30 may use any of the above described techniques individually, or in combination to modify operation of the tool 20 to account for deviations 110 between the commanded and actual states 20.

Additionally, it may be desirable to associate any of the aforementioned first and second paths 100, 100' to certain modes of operation for the system 10. For example, the system 10 may enable the manipulator 14 to interact with the site using manual and semi-autonomous modes of operation. An example of the semi-autonomous mode is described in U.S. Pat. No. 9,119,655, entitled, "Surgical Manipulator Capable of Controlling a Surgical Instrument in Multiple Modes," the disclosure of which is hereby incorporated by reference. In the semi-autonomous mode, the manipulator 14 directs movement of the tool 20 and, in turn, the energy applicator 24 at the surgical site. In one embodiment, the controller 30 models the tool 20 and/or energy applicator 24 as a virtual rigid body and determines forces and torques to apply to the virtual rigid body to advance and constrain the tool 20 and/or energy applicator 24 along any of the first and second paths 100, 100' in the semi-autonomous mode. Movement of the tool 20 in the semi-autonomous mode is constrained in relation to the virtual constraints generated by the boundary generator 66 and/or path generator 69.

In the semi-autonomous mode, the manipulator 14 is capable of moving the tool 20 free of operator assistance. Free of operator assistance may mean that an operator does not physically contact the tool 20 to apply force to move the tool 20. Instead, the operator may use some form of control to remotely manage starting and stopping of movement. For example, the operator may hold down a button of a remote control to start movement of the tool 20 and release the button to stop movement of the tool 20. Alternatively, the operator may press a button to start movement of the tool 20 and press a button to stop movement of the tool 20.

Alternatively, the system 10 may be operated in the manual mode. Here, in one embodiment, the operator manually directs, and the manipulator 14 controls, movement of the tool 20 and, in turn, the energy applicator 24 at the surgical site. The operator physically contacts the tool 20 to cause movement of the tool 20. The manipulator 14 monitors the forces and torques placed on the tool 20 by the operator in order to position the tool 20. A sensor that is part of the manipulator 14, such as a force-torque transducer, measures these forces and torques. In response to the applied forces and torques, the manipulator 14 mechanically moves the tool 20 in a manner that emulates the movement that would have occurred based on the forces and torques applied by the operator. Movement of the tool 20 in the manual mode is also constrained in relation to the virtual constraints generated by the boundary generator 66 and/or path generator 69.

For the "subsequent path" technique of FIGS. 7 and 8, the controller 30, in one example, commands movement of the tool 20 along the first path 100 according to the manual mode and commands movement of the tool 20 along the second path 100' according to the semi-autonomous mode. For example, it may be desirable to use the manual mode to control the tool 20 along the first path 100 for rough or bulk manipulation of the target tissue. In other words, the desire may be to quickly, but less accurately, remove large sections of the target tissue in the manual mode. Such bulk manipulation may result in relatively large deviations 110 between the commanded and actual states 98, 108. Accordingly, the semi-autonomous mode may be utilized to account for deviations 110 resulting from manual manipulation by commanding the tool 20 along the second path 100'. This scenario provides an automated and highly accurate follow-up or clean-up after manual manipulation.

For the "subsequent path" technique, the controller 30 may alternatively command movement of the tool 20 along both the first and second paths 100, 100' according to the semi-autonomous mode. For example, it may be desirable to use the semi-autonomous mode to control the tool 20 along the first path 100 for rough or bulk manipulation of the target tissue. In other words, the desire may be to quickly, but less accurately remove large sections of the target tissue. In one example, rough-cut paths may be designed for the most efficient bulk removal of material given the capability and workspace stability of the manipulator 14, without particular regard for accuracy. Thereafter, the semi-autonomous mode may again be utilized to account for deviations 110 from the first iteration of semi-autonomous manipulation by commanding the tool 20 along the second path 100'. Using the semi-autonomous mode in this fashion provides an iterative process for removing the target tissue, as described above. That is, any number of follow-up paths may be generated, thereby gradually removing the target tissue and gradually reducing the deviations 110 between commanded and actual states 98, 108 until a suitable state or threshold for the target tissue is achieved.

In other embodiments of this technique, the controller 30 is configured to command movement of the tool 20 along both the first and second paths 100, 100' according to the manual mode, in accordance with the techniques described above. Those skilled in the art appreciate that the controller 30 may command movement of the tool 20 along the first and second paths 100, 100' according to any other modes of operation and for other reasons not specifically recited herein For any of the embodiments shown in FIGS. 7-10, the system 10 may enable switching between the manual mode and the semi-autonomous mode at any time, and for any tool path. In one embodiment, such switching occurs in response to manual input. For example, the operator may use any suitable form of control to manage, e.g., remotely, which mode should be active. Alternatively, switching may be implemented autonomously in response to certain events or conditions. For example, the controller 30 may determine that the requisite amount of tissue has been removed in the manual mode and switch to the semi-autonomous mode in response. The controller 30 may further enable switching for the second tool path 100', to immediately correct the original tool path 100 or in anticipation of proactive correction of the original tool path 100. Furthermore, switching may occur based on analysis of the deviations 110 with respect to the threshold tolerance. Those skilled in the art appreciate that switching between manual and semi-autonomous modes may be performed according to other methods not explicitly described herein.

Several embodiments have been described in the foregoing description. However, the embodiments discussed herein are not intended to be exhaustive or limit the invention to any particular form. The terminology, which has been used, is intended to be in the nature of words of description rather than of limitation. Many modifications and variations are possible in light of the above teachings and the invention may be practiced otherwise than as specifically described.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

The invention claimed is:

1. A method of operating a robotic surgical system, the robotic surgical system comprising a surgical tool including a tool center point (TCP) and the surgical tool being configured to manipulate a target bone, a manipulator comprising a plurality of links and being configured to support the surgical tool, a navigation system comprising a localizer configured to monitor states of the manipulator and the target bone, and one or more controllers coupled to the manipulator and the navigation system, and with the method comprising the one or more controllers performing the steps of:

determining, using data from one or more of the manipulator and the navigation system, commanded states of the TCP for moving the surgical tool along a cutting path relative to the target bone for removing material from the target bone in preparation for an implant;

determining, using the data from one or more of the manipulator and the navigation system, actual states of the TCP responsive to commanded movement of the surgical tool along the cutting path relative to the target bone, wherein each one of the commanded states of the TCP has a corresponding one of the actual states of the TCP for a given time step;

comparing the corresponding commanded and actual states of the TCP for one or more given time steps for determining a deviation between the corresponding commanded and actual states; and based on an outcome of comparing the corresponding commanded and actual states of the TCP, modifying operation of the surgical tool to account for the deviation.

2. The method of claim 1, wherein modifying operation of the surgical tool comprises the one or more controllers modifying the cutting path to account for the deviation.

3. The method of claim 2, further comprising the one or more controllers:
predicting a future deviation between the future corresponding commanded and actual states based on past or present deviation; and
proactively modifying the cutting path to account for the predicted future deviation.

4. The method of claim 1, wherein modifying operation of the surgical tool comprises the one or more controllers modifying a feed rate of the surgical tool along the cutting path to account for the deviation.

5. The method of claim 4, further comprising the one or more controllers:
predicting a future deviation between the future corresponding commanded and actual states based on a past or present deviation; and
proactively modifying the feed rate of the surgical tool along the cutting path to account for the predicted future deviation.

6. The method of claim 1, wherein modifying of the surgical tool comprises the one or more controllers determining a new cutting path for the surgical tool to account for the deviation.

7. The method of claim 1, further comprising the one or more controllers:
obtaining the data from one or more of the manipulator and the navigation system, wherein the data is filtered according to a first filter length; and
determining, using the first filtered data, the commanded states of the TCP for moving the surgical tool along the cutting path relative to the target bone for removing material from the target bone in preparation for the implant.

8. The method of claim 7, further comprising the one or more controllers:
obtaining the data from one or more of the manipulator and the navigation system, wherein the data is unfiltered or filtered according to a second filter length being shorter than the first filter length; and
determining, using the unfiltered or second filtered data, the actual states of the TCP while commanding movement of the surgical tool along the cutting path relative to the target bone.

9. The method of claim 1, further comprising the one or more controllers:
generating a virtual boundary associated with the target bone, wherein the virtual boundary is for providing a constraint on the surgical tool;
determining the commanded states of the TCP for moving the surgical tool along the cutting path relative to virtual boundary associated with the target bone;
determining the actual states of the TCP while commanding movement of the surgical tool along the cutting path relative to the virtual boundary associated with the target bone; and
comparing the corresponding commanded and actual states of the TCP for one or more given time steps for determining the deviation between the corresponding commanded and actual states relative to the virtual boundary associated with the target bone.

10. A robotic surgical system comprising:
a surgical tool including a tool center point (TCP) and being configured to manipulate a target bone;
a manipulator comprising a plurality of links and being configured to support the surgical tool;
a navigation system comprising a localizer being configured to monitor states of the manipulator and the target bone; and
one or more controllers coupled to the manipulator and the navigation system and being configured to:
determine, using data from one or more of the manipulator and the navigation system, commanded states of the TCP to move the surgical tool along a cutting path relative to the target bone to remove material from the target bone in preparation for an implant;
determine, using the data from one or more of the manipulator and the navigation system, actual states of the TCP responsive to commanded movement of the surgical tool along the cutting path relative to the target bone, wherein each one of the commanded states of the TCP has a corresponding one of the actual states of the TCP for a given time step;
compare the corresponding commanded and actual states of the TCP for one or more given time steps to determine a deviation between the corresponding commanded and actual states; and
based on an outcome of comparing the corresponding commanded and actual states of the TCP, modify operation of the surgical tool to account for the deviation.

11. The robotic surgical system of claim 10, wherein the one or more controllers modify operation of the surgical tool by further being configured to modify the cutting path to account for the deviation.

12. The robotic surgical system of claim 11, wherein the one or more controllers are further configured to:
predict a future deviation between the future corresponding commanded and actual states based on a past or present deviation; and
proactively modify the cutting path to account for the predicted future deviation.

13. The robotic surgical system of claim 10, wherein the one or more controllers modify operation of the surgical tool by further being configured to modify a feed rate of the surgical tool along the cutting path to account for the deviation.

14. The robotic surgical system of claim 13, wherein the one or more controllers are further configured to:
predict a future deviation between the future corresponding commanded and actual states based on a past or present deviation; and
proactively modify the feed rate of the surgical tool along the cutting path to account for the predicted future deviation.

15. The robotic surgical system of claim 10, wherein the one or more controllers modify operation of the surgical tool by further being configured to determine a new cutting path for the surgical tool to account for the deviation.

16. The robotic surgical system of claim 10, wherein the one or more controllers are further configured to:
obtain the data from one or more of the manipulator and the navigation system, wherein the data is filtered according to a first filter length; and
determine, using the first filtered data, the commanded states of the TCP to move the surgical tool along the cutting path relative to the target bone to remove material from the target bone in preparation for the implant.

17. The robotic surgical system of claim 16, wherein the one or more controllers are further configured to:
  obtain the data from one or more of the manipulator and the navigation system, wherein the data is unfiltered or filtered according to a second filter length being shorter than the first filter length; and
  determine, using the unfiltered or second filtered data, the actual states of the TCP responsive to commanded movement of the surgical tool along the cutting path relative to the target bone.

18. The robotic surgical system of claim 10, wherein the one or more controllers are further configured to:
  generate a virtual boundary associated with the target bone, wherein the virtual boundary is configured to provide a constraint on the surgical tool;
  determine the commanded states of the TCP to move the surgical tool along the cutting path relative to the virtual boundary associated with the target bone;
  determine the actual states of the TCP responsive to commanded movement of the surgical tool along the cutting path relative to the virtual boundary associated with the target bone; and
  compare the corresponding commanded and actual states of the TCP for one or more given time steps to determine the deviation between the corresponding commanded and actual states relative to the virtual boundary associated with the target bone.

* * * * *